United States Patent [19]
Seidel et al.

[11] Patent Number: 5,814,517
[45] Date of Patent: *Sep. 29, 1998

[54] DNA SPACER REGULATORY ELEMENTS RESPONSIVE TO CYTOKINES AND METHODS FOR THEIR USE

[75] Inventors: H. Martin Seidel; I. Peter Lamb, both of San Diego, Calif.

[73] Assignee: Ligand Pharmaceuticals, Inc., San Diego, Calif.

[*] Notice: The term of this patent shall not extend beyond the expiration date of Pat. No. 5,707,803.

[21] Appl. No.: 410,779

[22] Filed: Mar. 27, 1995

Related U.S. Application Data

[63] Continuation-in-part of Ser. No. 228,935, Apr. 14, 1994, abandoned.

[51] Int. Cl.$^6$ .......................... C12N 15/85; C12N 15/11; C07H 21/04
[52] U.S. Cl. .................. 435/325; 435/69.1; 435/172.3; 435/320.1; 536/23.1; 536/23.2; 536/23.5; 536/24.1
[58] Field of Search ................................ 536/23.1, 23.2, 536/23.5, 24.1; 435/320.1, 69.1, 325, 172.3

[56] References Cited

U.S. PATENT DOCUMENTS 5,616,489   4/1997   Levy ....................................... 435/325

FOREIGN PATENT DOCUMENTS 0374503   6/1990   European Pat. Off. .
WO 95/08001   3/1995   WIPO .

OTHER PUBLICATIONS

Larigan et al., "Characterization of cDNA and genomic sequences encoding rabbit ELAM–1: conservation of structure and functional interactions with leukocytes", DNA Cell Biol. 11(2): 149–162, 1992.

Seidel et al., "Spacing of palindromic half sites as a determinant of selective STAT(signal transducers and activators of transcription) DNA binding and transcription activity", Proc. Natl. Acad. Sci. USA 92: 3041–3045, Mar. 1995.

Lamb et al., "STAT protein complexes activated by interferon–gamma and gp130 signaling molecules differ in their sequence preferences and transcription induction properties", Nucleic Acid Res. 23(16); 3283–3289, 1995.

Xu et al., "Regulation of transcription of immunoglobulin germ–line gamma1 RNA: analysis of the promoter/enhancer", EMBO J 11(1): 145–155, 1992.

Molecular Biology Reagents/Protocols 1992, United States Biochemical Corp., Cleveland, Ohio, 1991, p. 618, Oct. 1991.

Lew, D.; Decker, T.; Strehlow, I.; and Darnell, J., "Overlapping Elements in the Guanylate–Binding Protein Gene Promoter Mediate Transcriptional Induction by Alpha and Gamma Interferons," *Molecular and Cellular Biology*, vol. II, No. 01, pp. 182–191 (1991).

Decker, T.; Lew, D.; and Darnell, J., "Two Distinct Alpha–Interferon–Dependent Signal Transduction Pathways May Contribute to Activation of Transcription of the Guanylate–Binding Protein Gene," *Molecular and Cellular Biology*, vol. II, No. 10, pp. 5147–5153 (1991).

Decker, T.; Lew, D.; Mirkovitch, J.; and Darnell, J., "Cytoplasmic activation of GAF, an IFN–γ–regulated DNA–binding factor," *The EMBO Journal*, vol. 10, No. 4, pp. 927–932 (1991).

Akira, S.; Nishio, Y.; Inoue, M.; Wang, X.; Wei, S.; Matsusaka, T.; Yoshida, K.; Sudo, T.; Naruto, M; and Kishimoto, T., "Molecular Cloning of APRF, a Novel IFN–Stimulated Gene Factor 3 p91–Related Transcription Factor Involved in the gp 130–Meditated Signaling Pathway," *Cell*, vol. 77, pp. 63–71 (1994).

Hattori, M.; Abraham, L.; Northemann, W.; and Fey, G., "Acute–phase reaction induces a specific complex between hepatic nuclear proteins and the interleukin 6 response element of the rat $\alpha_2$–macroglobulin gene," *Proc. Natl. Acad. Sci. USA*, vol. 87, pp. 2364–2368 (1990).

Wegenka, U.; Buschmann, J.; Lütticken, C.; Heinrich, P.; and Horn, F., "Acute–Phase Response Factor, a Nuclear Factor Binding to Acute–Phase Response Elements, is Rapidly Activated by Interleukin–6 at the Posttranslational Level," *Molecular and Cellular Biology*, vol. 13, No. 1, pp. 276–288 (1993).

Ito, T.; Tanahashi, H.; Misumi, Y.; and Sakaki, Y., "Nuclear factors interacting with an interleukin–6 responsive element of a rat $\alpha_2$–macroglobulin gene," *Nucleic Acids Research*, vol. 17, No. 22, pp. 9425–9435 (1989).

Hocke, G.; Barry, D.; and Fey, G., "Synergistic Action of Interleukin–6 and Glucocorticoids Is Mediated by the Interleukin–6 Response Element of the Rat $\alpha_2$–Macroglobulin Gene," *Molecular and Cellular Biology*, vol. 12, No. 5, pp. 2282–2294 (1992).

Yuan, J.; Wegenka, U.; Lütticken, C.; Buschmann, J.; Decker, T.; Schindler, C.; Heinrich, P.; and Horn, F., "The Signalling Pathways of Interleukin–6 and Gamma Interferon Converge by the Activation of Different Transcription Factors Which Bind to Common Responsive DNA Elements," *Molecular and Cellular Biology*, vol. 14, No. 3, pp. 1657–1668 (1994).

(List continued on next page.)

Primary Examiner—Jasemine C. Chambers
Assistant Examiner—Scott D. Priebe
Attorney, Agent, or Firm—J. Scott Elmer; William L. Respess

[57] ABSTRACT

The present invention provides oligonucleotide sequences comprising DNA regulatory elements of the general sequence TTN$_X$AA that bind activated transcriptional regulatory proteins in response to signaling molecules, such as cytokines. Further, the present invention also provides DNA constructs comprising the oligonucleotide sequences, cells transfected with the DNA constructs, and methods of using the DNA constructs and transfected cells to provide for the controlled expression of structural genes, for the detection and recovery of transcriptional regulatory proteins, and for measuring the ability of compounds to act as agonist and antagonists of gene transcription.

19 Claims, 2 Drawing Sheets

OTHER PUBLICATIONS

Kunz, D.; Zimmermann, R.; Heisig, M.; and Heinrich, P., "Identification of the promoter sequences involved in the interleukin–6 dependent expression of the rat $\alpha_2$–macroglobulin gene," *Nucleic Acids Research*, vol. 17, No. 3, pp. 1121–1138 (1989).

Khan, K.; Lindwall, G.; Maher, S.; and Bothwell, A., "Characterization of Promoter Elements of an Interferon–Inducible Ly–6E/A Differentiation Antigen, Which Is Expressed on Activated T Cells and Hematopoietic Stem Cells," *Molecular and Cellular Biology*, vol. 10, No. 10, pp. 5150–5159 (1990).

Khan, K.; Shuai, K.; Lindwall, G.; Maher, S.; Darnell, J.; and Bothwell, A., "Induction of the Ly–6A/E gene by interferon $\alpha/\beta$ and $\gamma$ requires a DNA element to which a tyrosine–phosphorylated 91–kDa protein binds," *Proc. Natl. Acad. Sci. USA*, vol. 90, pp. 6806–6810 (1993).

Sadowski, H. and Gilman, M., "Cell–free activation of a DNA–binding protein by epidermal growth factor," *Nature*, vol. 362, pp. 79–83 (1993).

Wagner, B.; Hayes, T.; Hoban, C.; and Cochran, B., "The SIF binding element confers sis/PDGF inducibility onto the c–fos promoter," *The EMBO Journal*, vol. 9., No. 13, pp. 4477–4484 (1990).

Strehlow, I. and Decker, T., "Transcriptional induction of IFN–$\gamma$–responsive genes is modulated by DNA surrounding the interferon stimulation response element," *Nucleic Acids Research*, vol. 20, No. 15, pp. 3865–3872 (1992).

Wong, P.; Severns, C.; Guyer, N.; and Wright, T., "A Unique Palindromic Element Mediates Gamma Interferon Induction of mig Gene Expression," *Molecular and Cellular Biology*, vol. 14, No. 2, pp. 914–922 (1994).

Silvennoinen, O.; Schindler, C.; Schlessinger, J.; and Levy, D., "Ras–Independent Growth Factor Signaling by Transcription Factor Tyrosine Phosphorylation," *Science*, vol. 261, pp. 1736–1739 (1993).

Ruff–Jamison, S.; Chen, K.; and Cohen, S., "Induction by EGF and Interferon–$\gamma$ of Tyrosine Phosphorylated DNA Binding Proteins in Mouse Liver Nuclei," *Science*, vol. 261, pp. 1733–1736 (1993).

Larner, A.; David, M.; Feldman, G.; Igarashi, K.; Hackett, R., Webb, D.; Sweitzer, S.; Petricoin, E.; and Finbloom, D., "Tyrosine Phosphorylation of DNA Binding Proteins by Multiple Cytokines," *Science*, vol. 261, pp. 1730–1733 (1993).

Shuai, K.; Stark, G.; Kerr, I.; and Darnell, J., "A Single Phosphotyrosine Residue of Stat91 Required for Gene Activation by Interferon–$\gamma$," *Science*, vol. 261, pp. 1744–1746 (1993).

Sadowski, H.; Shuai, K., Darnell, J.; and Gilman, M., "A Common Nuclear Signal Transduction Pathway Activated by Growth Factor and Cytokine Receptors," *Science*, vol. 261, pp. 1739–1744 (1993).

Kanno, Yuka; Kozak, C.; Schindler, C.; Driggers, P.; Ennist, D.; Gleason, S.; Darnell, J.; and Ozato, K., "The Genomic Structure of the Murine ICSBP Gene Reveals the Presence of the Gamma Interferon–Responsive Element, to Which an ISGF3$\alpha$ Subunit (or Similar) Molecule Binds," *Molecular and Cellular Biology*, vol. 13, No. 7, pp. 3951–3963 (1993).

Harroch, S.; Revel, M.; and Chebath, J., "Induction by interleukin–6 of interferon regulatory factor 1 (IRF–1) gene expression through the palindromic interferon response element pIRE and cell type–dependent control of IRF–1 binding to DNA," *The EMBO Journal*, vol. 13, No. 8, pp. 1942–1949 (1994).

Sims, S.; Cha, Y.; Romine, M.; Gao, P.; Gottlieb, K.; and Deisseroth, A., "A Novel Interferon–Inducible Domain: Structural and Functional Analysis of the Human Interferon Regulatory Factor 1 Gene Promoter," *Molecular and Cellular Biology*, vol. 13, No. 1, pp. 690–702 (1993).

Pearse, R.; Feinman, R.; Shuai, K.; Darnell, J.; and Ravetch, J., "Interferon $\gamma$–induced transcription of the high–affinity Fc receptor for IgG requires assembly of a complex that includes the 91–kDa subunit of transcription factor ISGF3," *Proc. Natl. Acad. Sci. USA*, vol. 90, pp. 4314–4318 (1993).

Pearse, R.; Feinman, R.; and Ravetch, J., "Characterization of the promoter of the human gene encoding the high affinity IgG receptor: Transcriptional induction by $\gamma$–interferon is mediated through common DNA response elements," *Proc. Natl. Acad. Sci. USA*, vol. 88, pp. 11305–11309 (1991).

Kotanides, H. and Reich, N., "Requirement of Tyrosine Phosphorylation for Rapid Activation of a DNA Binding Factor by IL–4," *Science*, vol. 262, pp. 1265–1267 (1993).

Schindler, C.; Kashleva, H.; Pernis, A.; Pine, R.; and Rothman, P., "STF–IL–4: a novel IL–4–induced signal transducing factor," *The EMBO Journal*, vol. 13, No. 6, pp. 1350–1356 (1994).

Li, P.; He, X.; Gerrero, M.; Mok, M.; Aggarwal, A.; and Rosenfeld, M., "Spacing and oriention of bipartite DNA–binding motifs as potential functional determinants for POU domain factors," *Genes & Development*, vol. 7, pp. 2483–2496 (1993).

Carlberg, C., "RXR–Independent Action of the Receptors for Thyroid Hormone, Retinoid Acid and Vitamin D on Inverted Palindromes," *Biochemical and Biophysical Research Communications*, vol. 195, No. 3, pp. 1345–1353 (1993).

Mangelsdorf, D., et al., "Retinoid Receptors," *The Retinoids: Biology, Chemistry and Medicine*, 2nd ed., pp. 331–332 (1994).

Umesono, K.; Murakami, K.; Thompson, C.; and Evans, R., "Direct Repeats as Selective Response Elements for the Thyroid Hormone, Retinoic Acid, and Vitamin $D_3$ Receptors," *Cell*. vol. 65, pp. 1255–1266 (1991).

Näär, A.; Boutin, J.; Lipkin, S.; Yu, V.; Holloway, J.; Glass, C.; and Rosenfeld, M., "The Orientation and Spacing of Core DNA–Binding Motifs Dictate Selective Transcriptional Responses to Three Nuclear Receptors," *Cell*, vol. 65, pp. 1267–1279 (1991).

Reid, L.; Brasnett, A.; Gilbert, C.; Porter, A.; Gewert, D.; Stark, G.; and Kerr, I., "A single DNA response element can confer inducibility to both $\alpha$– and $\gamma$–interferons," *Proc. Natl. Acad. Sci. USA*, vol. 86, pp. 840–844 (1989).

Wakao, H.; Gouilleux, F., and Groner, B., "Mammary gland factor (MGF) is a novel member of the cytokine regulated transcription factor gene family and confers the prolactin response," *The EMBO Journal*, vol. 13, No. 9, pp. 2182–2191 (1994).

Mui, A., Wakao, H., O'Farrell, A., Harada, N., and Miyajima, A., "Interleukin–3, granulocyte–macrophage colony stimulating factor and interleukin–5 transduce signals through two STAT5 homologs," *The EMBO Journal*, vol. 14, No. 6, pp. 1166–1174 (1995).

Drachman, J., Griffin, J., and Kaushansky, K., "The c–Mpl Ligand (Thrombopoietin) Stimulates Tyrosine Phosphorylation of Jak2, Shc, and c–Mpl," *The Journal of Biological Chemistry*, vol. 270, No. 10, pp. 4979–4982 (1995).

Beadling, C., Guschin, D., Witthuhn, B., Ziemiecki, A., Ihle, J., Kerr, I., and Cantrell, D., "Activation of JAK kinases and STAT proteins by interleukin–2 and interferon α, but not the T cell antigen receptor, in human T lymphocytes," *The EMBO Journal*, vol. 13, No. 23, pp. 5605–5615 (1994).

Gouilleux, F., Wakao, H., Mundt, M., and Groner, B., "Prolactin induces phosphorylation of Tyr694 of Stat5 (MGF), a prerequisite for DNA binding and induction of transcription," *The EMBO Journal*, vol. 13, No. 18, pp. 4361–4369 (1994).

Standke, G., Meier, V., and Groner, B., "Mammary Gladn Factor Activated by Prolactin in Mammary Epithelial Cells and Acute–Phase Response Factor Activated by Interleukin–6 in Liver Cells Share DNA Binding and Transactivation Potential," *Molecular Endocrinology*, vol. 8, No. 4, pp. 469–477 (1994).

Delphin, S., and Stavnezer, J., "Characterization of an Interleukin 4(IL–4) Responsive Region in the Immunoglobulin Heavy Chain Germline & Promoter; Regulation by NF–IL–4, a C/EBP Family Member and NF–κB/p50," *J. Exp. Med.*, vol. 181, pp. 181–192 (1995).

Albrecht, ., Peiritsch, S., and Woisetschläger, M., "A bifunctional control element in the human lgE germline promoter involved in repression and IL–4 activation," *International Immunology*, vol. 6, No. 8, pp. 1143–1151 (1994).

Coffer, P., Lutticken, C., Puijenbroek, A., Jonge, M., Horn, F., and Kruijer, W., "Transcriptional regulation of the junB promoter: analysis of STAT–mediated signal transduction," *Oncogene*, vol. 10(5) pp. 985–994 (1995).

Fujitani, Y., Nakajima, K., Kojima, H., Nakae, K., Takeda, ., and Hirano, T., "Transcriptional Activation of the IL–6 Response Element in the JunB Promoter is Mediated by Multiple STAT Family Proteins," *Biochemical and Biophysical Research Communications*, vol. 202, No. 2, pp. 1181–1187 (1994).

Hou, J., Schindler, U., Henzel, W., Ho, T., Brasseur, M., and McKnight, S., "An Interleukin–4–Induces Transcription Factor: IL–4 STAT," *Science*, vol. 265, pp. 1701–1706 (1994).

Rothman, P.; Kreider, B.; Azam, M.; Levy, D.; Wegenka, U.; Eilers, A.; Decker, T.; Horn, F.; Hashleva, H.; Ihle, J.; and Schindler, C., "Cytokines and Growth Factors Signal Through Tyrosine Phosphorylation of a Family of Related Transcription Factors," *Immunity*, vol. 1 pp. 457–468 (1994).

Lamb, P.; Kessler, L. V.; Suto, C.; Levy, D.E.; Deisdel, H.M.; Stein, R.B.; and Rosen, J., "Rapid Activation of Proteins that Interact with the Interferon–γ Activation Site in Response to Multiple Cytokines" *Blood*, vol. 83, No. 8, pp. 2063–2071 (1994).

Yoon, J.; Berry, S.; Seelig, S.; and Towle, H., "An Inducible Nuclear Factor Binds to a Growth Hormone–regulated Gene," *The Journal of Biological Chemistry*, vol. 265, No. 32, pp. 19947–19954 (1990).

Pierre, S.; Jolivet G., Devinoy, E.; Théron, M.; Maliénou–N'Gassa, R.; Puissant, C.; and Houdebine, L., "A distal region enhances the prolactin induced promoter activity of the rabbit αs1–casein gene," *Molecular and Cellular Endocrinology*, vol. 87, pp. 147–156 (1992).

Doppler, W.; Villunger, A.; Jennewein, P.; Brduscha, K.; Groner, B.; and Ball, R., "Lactogenic Hormone and Cell Type–Specific Control of the Whey Acidic Protein Gene Promoter in Transfected Mouse Cells," *Molecular Endocrinology*, vol. 5, No. 11, pp. 1624–1632 (1991).

Köhler, I.; and Rieber, E., "Allergy–associated Iε and Fcε receptor II (CD23b) genes activated via binding of an interleukin–4–induced transcription factor to a novel Responsive Element," *Eur. J. Immunol.*, vol. 23, pp. 3066–3071 (1993).

Rothman, P.; Li, S.; Gorham, B.; Glimcher, L.; Alt, F.; and Boothby, M., "Identification of a Conserved Lipopolysaccharide–Plus–Interleukin–4–Responsive Element Located at the Promoter of Germ Line ε Transcripts," *Molecular and Cellular Biology*, vol. 11, No. 11, pp. 5551–5561 (1991).

Ichiki, T.; Takahashi, W.; and Watanabe, T., "Regulation of the Expression of Human Cε Germline Transcript," *The Journal of Immunology*, vol. 150, No. 12, pp. 5408–5417 (1993).

Pearse, R.; Feinman, R.; and Ravetech, J. "Characterization of the promoter of the human gene encoding the high–affinity IgG receptor: Transcriptional induction by γ–interferon is mediated through common DNA response elements," *Proc. Natl. Acad. Sci USA*, vol. 88, pp. 11305–11309 (1991).

Wegenka, U.; Buschmann, J.; Lütticken, C.; Heinrich, P.; and Horn, F., "Acute–Phase Response Factor, a Nuclear Factor Binding to Acute–Phase Response Elements, Is Rapidly Activated by Interleukin–6 at the Posttranslational Level," *Molecular and Cellular Biology*, vol. 13, No. 1, pp. 276–288 (1993).

Yuan, J.; Wegenka, U.; Lütticken, C.; Buschmann, J.; Decker, T.; Schindler, C.; Heinrich, P.; and Horn, F., "The Signalling Pathways of Interleukin–6 and Gamma Interferon Converge by the Activation of Different Transcriptional Factors Which Bind to Common Responsive DNA Elements," *Molecular and Cellular Biology*, vol. 14, No. 3, pp. 1657–1668 (1994).

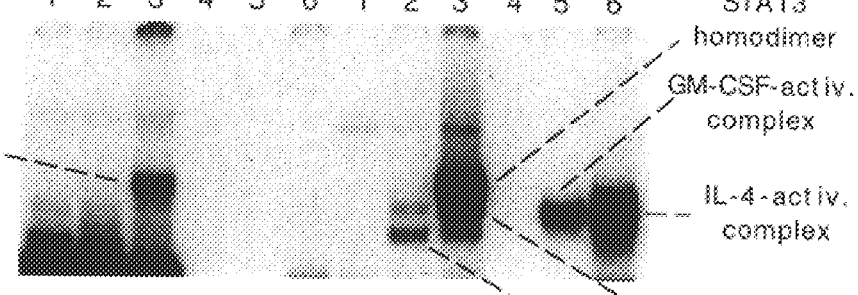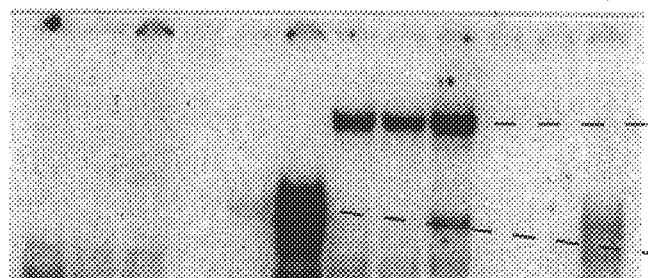

DNA SPACER REGULATORY ELEMENTS RESPONSIVE TO CYTOKINES AND METHODS FOR THEIR USE

This is a continuation-in-part of application Ser. No. 08/228,935 filed on Apr. 14, 1994, now abandoned.

FIELD OF THE INVENTION

This invention relates to oligonucleotide sequences that bind regulatory proteins that affect transcription in response to various molecules, such as cytokines, to DNA constructs comprising the oligonucleotide sequences, cells transfected with the DNA constructs, and to methods of using the same to provide for the controlled expression of heterologous genes, for the detection and recovery of new regulatory proteins, and for measuring the ability of compounds to act as agonist and antagonists of gene transcription.

BACKGROUND OF THE INVENTION

In many cellular systems, extracellular signaling molecules, such as polypeptide ligands, bind to receptors on the surface of the cells, thereby triggering an intracellular signaling pathway that ultimately regulates gene transcription within the cells. For example, cytokines and growth factors, which comprise a large and diverse family of soluble polypeptides that control the growth, differentiation and function of mammalian cells, bind to specific cell surface receptors, that in some way transduce signals that elicit a specific phenotypic response. A. Miyajama et al., 10 *Annu. Rev. Immunol.*, 295 (1992); M. Aguet et al., 55 *Cell*, 273 (1988); T. Kishimoto et al., 258 *Science*, 593 (1992) and A. Ullrich and J. Schlessinger, 61 *Cell*, 203 (1990). Abundant evidence shows that changes in the transcription rate of specific genes are an important component of this response. This is thought to be a consequence of alterations in the amount or the activity of specific DNA-binding proteins.

In some instances, progress has been made in defining the pathway that leads from a receptor-ligand interaction at the cell surface to changes in the activity of such DNA binding proteins or other nuclear proteins. Ulrich, 61 *Cell* 203. In this regard, a common response in surface receptor signaling pathways involves the activation of Ras. L. S. Mulcahy et al., 313 *Nature*, 241 (1985). Activated Ras then initiates a cascade of serine/threonine phosphorylations through MAP kinases leading to phosphorylation of DNA binding proteins, thereby changing their transcriptional modulatory activity. S. A. Moodie et al., 260 *Science*, 1658 (1993); C. A. Lange-Carter et al., 260 *Science*, 315 (1993); C. S. Hill et al., 73 *Cell* 395 (1993); H. Gille et al., 358 *Nature*, 414 (1992) and R. H. Chen et al., 12 *Mol. Cell. Biol.*, 915 (1992).

Despite these advances, the signal transduction pathways utilized by many growth factors and cytokines to alter gene expression remain unclear. Thus, although known second messengers have been implicated in signal transduction in response to some of these factors, their role in modulating gene expression remains speculative. Miyajama, 10 *Annu. Rev. Immunol.*, 295 and D. E. Levy and J. E. Darnell, 2 *New Biol.*, 923 (1990). This in turn raises the question of how ligand specific responses are elicited in such cellular systems. Ullrich, 61 *Cell* 203; M. V. Chao, 68 *Cell*, 995 (1992) and Levy, 2 *New Biol.*, 923.

Progress in resolving these issues has been made recently in the interferon (IFN) system. IFNs α and β (type I) act as a primary non-specific defense against viral infections. S. Petska and J. A. Langer, 56 *Annu. Rev. Biochem.*, 727 (1987). IFNγ (type II) has anti-viral properties but also plays a major role in regulation of the immune response. Id. Type I and type II IFNs bind to distinct cell surface receptors and cause rapid alterations in gene expression. Aguet, 55 *Cell*, 273; Uze, 60 *Cell*, 225; and G. C. Sen and P. Lengyel, 267 *J. Biol. Chem.*, 5017 (1992). Specific sequence elements have been identified in the promoters of genes that respond to IFNα, termed interferon-α stimulated response elements (ISREs), that are both necessary and sufficient for regulation by IFNα. Sen, 267 *J. Biol. Chem.*, 5017. Specifically, activation of the IFNα receptors stimulates tyrosine phosphorylation of a family of proteins that serve as DNA binding proteins, and accordingly as transcription regulatory factors via the ISRE. C. Schindler et al., 257 *Science*, 809 (1992); K. Shuai et al., 258 *Science*, 1808 (1992) and M. J. Gutch et al., 89 *Proc. Natl. Acad. Sci. USA*, 11411 (1992). These DNA binding proteins, generically termed "signal transducers and activators of transcription" (STATs), assemble into a multimeric complex, translocate to the nucleus, and bind cis-acting acting enhancer elements in the appropriate regulatory regions. D. E. Levy et al., 3 *Genes Dev.*, 1362 (1989); and D. S. Kessler et al., 4 *Genes Dev.*, 1753 (1990) and Z. Zhong et al., 264 Science, 95 (1994).

One example of an IFNα-induced ISRE binding protein complex is ISGF3. T. C. Dale et al., 86 *Proc. Natl. Acad. Sci.*, 1203 (1989) and X-Y. Fu et al., 87 *Proc. Natl. Acad. Sci.*, 8555 (1990). ISGF3 is a complex of 4 binding proteins, called p48, p84 (STAT1α), p91 (STAT1α) and p113 (STAT2). Recently, cDNAs encoding the proteins that constitute ISGF3 have been isolated and characterized. X-Y Fu et al., 89 *Proc. Natl. Acad. Sci.*, 7840 (1992); C. Schindler et al., 89 *Proc. Natl. Acad. Sci.*, 7836 (1992) and S. A. Veals et al., 12 *Mol. Cell. Biol.*, 3315 (1992). p48 is the DNA binding component of ISGF3 and has homology to myb. Veals, 12 *Mol. Cell. Biol.*, 3315. p84 and p91 are probably alternatively spliced products of the same gene and are related to p113. X-Y Fu, 89 *Proc. Natl. Acad. Sci.*, 7840 and Schindler, 89 *Proc. Natl. Acad. Sci.*, 7836. p84, p91 and p113 are novel proteins that contain SH2 and SH3 domains and are found in the cytoplasm of untreated cells. Schindler, 257 *Science*, 809 and X.Y. Fu, 70*Cell*, 323–335 (1992). Thus, IFNα treatment of cells results in rapid tyrosine phosphorylation of p84, p91 and p113, causing them to associate and form a heteromeric complex with p48 to form ISGF3, which then translocates to the nucleus and binds to ISREs, stimulating transcription. Id.; Dale, 86 *Proc. Natl. Acad. Sci.*, 1203 and Kessler, 4 *Genes Dev.*, 1753.

Regulation in response to IFNγ is conferred by a distinct sequence from the ISRE, the gamma activated sequence (GAS). T. Decker et al., 10 *EMBO J.*, 927 (1991); K. D. Khan et al., 90 *Proc. Natl. Acad. Sci.*, 6806 (1993) and D. J. Lew et al., 11 *Mol. Cell. Biol.*, 182 (1991). Treatment of cells with IFNγ results in tyrosine phosphorylation of p91 (STAT1α), which then translocates to the nucleus and binds to the GAS. Decker, 10 *EMBO J,.* 927 and K. Shuai et al., 258 *Science*, 1808 (1992). Thus the specificity of binding of either IFNα or IFNγ to their receptors is translated into a specific phosphorylation pattern within a related family of latent transcription factors (i.e. DNA binding proteins). This pattern of phosphorylation dictates the association state of the proteins, which determines specificity of binding to either an ISRE or a GAS, and the subsequent transcriptional response.

Yet another cytokine, Interleukin-6 (IL-6) plays a major role in the induction of the acute phase response in hepatocytes. The acute phase response is characterized by the dramatic transcriptional upregulation of a distinct set of genes, termed acute phase response genes. P. C. Heinrich et al, 265 *Biochem. J.*, 621–636 (1990). Studies of the promoter regions of these genes have identified specific DNA sequences that are required for induction of acute phase response genes by IL-6. See D. R. Kunz et al., 17 *Nuc. Acids Res.*, 1121–1138 (1989); M. Hattori et al., 87 *Proc. Natl. Acad. Sci USA,* 2364–2368 (1990); K. A. Won and H. Baumann, 10 *Mol. Cell. Biol.*, 3965–3978 (1990) and D. R. Wilson et al., 10 *Mol. Cell. Biol.*, 6181–6191 (1990). These sequences are termed acute phase response elements (APREs). One type of APRE shows many similarities to the GAS elements that confers induction by IFNγ. Yuan et al., 14 *Mol. Cell. Biol.*, 1657–1668 (1994). Proteins that bind to this class of APREs have been characterized and purified. U. M. Wegenka et al., 13 *Mol. Cell. Biol.*, 276–288 (1993); T. Ito et al., 17 *Nuc. Acids Res.*, 9425–9435 (1989) and Hattori, 87 *Proc. Natl. Acad. Sci. USA,* 2364–2368. A cDNA clone encoding the IL-6-induced APRE-binding protein has been isolated (Zhong, 264 *Science,* 95; Akira et al., 77*Cell* 63–71 (1994); Zhong, et al., 91 *Proc. Natl. Acad. Sci.,* 4806–4810 (1994); Raz et al., 269 *J. Biol. Chem.*, 24391–24395 (1994)), and was found to encode a protein that shows considerable homology to p91 (STAT1α). For this reason the protein is termed STAT3. Like STAT1α, STAT3 is a latent transcription factor that is activated to bind DNA by rapid tyrosine phosphorylation.

Interleukin-4 (IL-4) is a pleiotropic cytokine that elicits biological responses in a variety of both lymphoid and non-lymphoid cell types. IL-4 is a glycoprotein of approximately 19 kD produced primarily by the Th2 subset of activated T-cells. IL-4 has since been shown to play an important role in B-cell proliferation, the regulation of immunoglobulin expression, in T-cell regulation and in the growth and differentiation of hematopoietic precursor cells. IL-4 exerts its biological effects through a specific high-affinity receptor on the surface of hematopoietic as well as certain non-hematopoietic cell lines. One chain of its receptor, the γc chain, is shared by the IL-2, IL-7, IL-9, IL-13 and IL-15 receptors. M. Kondo et al., 262 *Science* 1874 (1993), M. Noguchi et al., 262 *Science* 1877 (1993), S. Russell et al., 262 *Science* 1880 (1993), and M. Kondo et al., 263 *Science* 1453 (1994).

Binding of IL-4 to its receptor on the cell surface results in the activation of an intracellular tyrosine kinase and the rapid phosphorylation of several proteins on tyrosine. These initial events appear to be directly related to the immediate effects of IL-4 on target gene transcription. In particular, IL-4 up-regulates in responsive cell lines the expression of several cell-surface antigens including class II MHC, the low affinity Fc receptor for IgE (FcεRII, CD23), LFA-1 and LFA-3, CD40 and surface IgM. B. Aggarwal and J. U. Gutterman, *Human Cytokines: Handbook for Basic Chemical Research* Blackwell Scientific Publications, Boston, Mass. (1992). Perhaps the most prominent role of IL-4 is in B-cell differentiation, where IL-4 acts as a "switch factor" promoting an Ig heavy chain class switch to IgE, the major mediator of Type I allergic reactions. W. E. Paul, 77 *Blood* 1859 (1991). Evidence that IL-4 operates through a STAT signal transduction system is based upon the observation that IL-4 rapidly activates in a variety of cell lines phosphotyrosine-containing protein complexes that bind to a GAS-like DNA sequence element. H. Kotanides and N. Reich 262 *Science* 1265 (1993) and C. Schindler et al., 13 *EMBO J.* 1350 (1994); P. Lamb et al., 83 Blood, 2063 (1994) and I. Köhler and E. P. Rieber, 23 *Eur. J. Immunol.*, 3066 (1993). A STAT activated by IL-4 in THP-1 cells has been cloned recently (called STAT-IL-4 or STAT6) and is likely a constituent of the reported IL-4 induced complexes. J. Hou et al., 265 *Science,* 1701 (1994) and J. N. Ihle et al., 11 *Trends in Genetics,* 69 (1995).

Interleukin 13 (IL-13) is a pleiotropic cytokine that shares many of the biological activities of IL-4. G. Zurawski and J. E. de Vries, 15 *Immunol. Today* 19 (1994). IL-13 has roughly 30% sequence identity with IL-4 and exhibits IL-4-like activities on monocytes/macrophages and B-cells (A. Minty et al., 362, *Nature* 248 (1993) and A. N. J. McKenzie et al., 90 *Proc. Natl. Acad. Sci. USA* 3735 (1993). However, unlike IL-4, IL-13 has no effect on T-cells. The biological activity of IL-13 is mediated through binding to its specific high-affinity cell surface receptors consisting of an IL-13 binding subunit and one or more receptor components that are shared with the IL-4 receptor (the 'IL-4R' subunit and/or the γc subunit). G. Aversa et al., 178 *J. Exp. Med.* 2213 (1993). Evidence that IL-13, like IL-4, operates through a STAT signal transduction system is based upon the observation that IL-13 rapidly activates phosphotyrosine-containing protein complexes very similar to those induced by IL-4 that bind to a GAS-like DNA sequence element . I. Köhler et al., 345 *FEBS Lett.* 187 (1994).

GM-CSF belongs to a group of growth factors termed colony stimulating factors which are involved in the survival, clonal expansion, and differentiation of hematopoietic progenitor cells. J. Gasson, 77 *Blood* 1131 (1991) and N. A, Nicola, 58 *Annu Rev. Biochem.* 45 (1989). GM-CSF acts on a set of partially committed progenitor cells and causes them to divide and differentiate in the granulocyte-macrophage pathways. GM-CSF can also activate mature granulocytes and macrophages. In addition to effects on myelomonocytic lineages, GM-CSF can promote the proliferation of erythroid and megakaryocyte progenitor cells. GM-CSF, an 18–22 kD glycoprotein, is produced by a variety of cells, including T-cells, B-cells, macrophages, mast cells, endothelial cells and fibroblasts, in response to immune or inflammatory stimuli.

GM-CSF exerts its effects by interacting with cell surface receptors on specific target cells. The receptor is composed of two chains, GM-CSF-α and GM-CSF-β. L. S. Park et al., 89 *Proc. Natl. Acad. Sci.* 4295 (1992). The GM-CSF-α is specific to GM-CSF, while the GM-CSF-β is identical to the β subunit of the IL-5 and IL-3 receptors. G. Goodall et al., 8 *Growth Factors* 87 (1993). Although neither GM-CSFα or GM-CSFβ have intrinsic kinase activity, GM-CSF treatment of cells results in rapid tyrosine phosphorylation of multiple proteins. Evidence that GM-CSF operates through a STAT signal transduction system is based upon the observation that GM-CSF rapidly activates in a variety of cell lines phosphotyrosine-containing protein complexes that bind to a GAS-like DNA sequence element. A. C. Larner et al., 261 *Science* 1730 (1993) and P. Lamb et al., 83 *Blood* 2063 (1994). It has been reported that GM-CSF activates STAT5, which thus may be a constituent of the reported GM-CSF activated complexes. Ihle et al., 11 *Trends in Genetics,* 69 (1995).

Interleukin-3 (IL-3) is a pleiotropic cytokine produced primarily by activated T-cells. Its effects include stimulating the proliferation and differentiation of both pluripotent hematopoietic precursor cells as well a wide variety of lineage committed cells Ihle, J. N. in *Peptide Growth Factors and their Receptors* Springer-Verlag, N.Y. (1991). The mature protein has an apparent molecular weight of 28,000, and binds to a cell surface receptor (IL-3R) that consists of at least two polypeptide chains, IL-3Rα and IL-3Rβ. The IL-3Rβ chain is also a component of the IL-5 and GM-CSF receptors, whereas the IL-3α chain is unique to the IL-3R. Miyajama et al 82 *Blood* 1960, (1993). Binding of IL-3 to its receptor causes the activation of the tyrosine kinase JAK2 and the rapid tyrosine phosphorylation of a set of cytoplasmic proteins. O. Silvennoinen et al., 90 *Proc. Natl. Acad Sci.* 8429 (1993). A GAS-binding complex that contains a member of the STAT family can be detected in extracts from cells treated with IL-3. A. C. Larner et al., 261 *Science* 1730 (1993); J. N. Ihle et al., 19 *Trends Biochem. Sci.* 222 (1994). It has been reported that IL-3 activates STAT5, which thus may be a constituent of the reported IL-3-activated complexes. J. N. Ihle et al., 11 *Trends in Genetics,* 69 (1995).

Erythropoietin (Epo) is the major hormone responsible for the proliferation and maturation of red blood cell precursors. S. B. Krantz, 77 *Blood* 419 (1991). In vitro evidence indicates that it also plays a role in thrombocytopoiesis. An et al., 22 *Exp. Hemat.* 149 (1994). The protein, which has an apparent molecular weight of 30,000, is produced mainly in the kidneys and is induced by conditions of tissue hypoxia. It acts by binding to a cell surface receptor (EpoR) that consists of a single polypeptide chain that is a member of the hematopoietin receptor family. A. D'Andrea et al 57 *Cell* 277 (1989). An early event following the binding of Epo to EpoR is the activation of the tyrosine kinase JAK2, which associates non-covalently with the cytoplasmic domain of the receptor chain. B. Witthuhn et al, 74 *Cell* 227. Activation of JAK2 by Epo is correlated with induction of tyrosine phosphorylation of the EpoR and cytoplasmic proteins. Epo treatment of cells also results in the rapid induction of a GAS-binding activity that contains as yet unidentified STAT proteins, that are thought to contribute to Epo-induced changes in gene expression. P. Lamb et al., 83 *Blood* 2063 (1994); Finbloom et al., 14 *Mol. Cell Biol.* 2113 (1994). It has been reported that Epo activates STAT5, which thus may be a constituent of the reported Epo-activated complexes. J. N. Ihle et al., 11 *Trends in Genetics,* 69 (1995).

G-CSF is a pleiotropic cytokine best known for its specific effects on the proliferation, differentiation, and activation of hematopoietic cells of the neutrophilic granulocyte lineage. G-CSF has also been reported to have chemotactic activity for human granulocytes and monocytes as well as for mesenchymal cells including fibroblasts, smooth muscle cells and myofibroblasts. These in vitro functions reflect the potential in vivo roles for G-CSF in the maintenance of steady state hemotopoiesis, defense against infection, inflammation and repair. When G-CSF was administered to various animal models, an elevation of circulating neutrophils has been observed. G-CSF is now used clinically in patients that have granulopenia as a result of receiving chemotherapy or receiving immunosuppressive agents after organ transplantation. M. A. S. Moore, 9 *Annu. Rev. Immunol.* 159 (1991), N. A. Nicola, 58 *Annu. Rev. Biochem.* 45 (1989), and E. Pimentel, (1994) in *Handbook of Growth Factors Vol III*, E. Pimentel, ed., CRC Press, Boca Raton, p. 177.

G-CSF exerts its biological activity through binding to G-CSFr. The receptor for G-CSF (G-CSFr) is a member of the type I cytokine receptor superfamily that lacks a kinase domain and appears to consist of a single polypeptide chain . Dimerization of two G-CSFr chains forms a high affinity binding site for G-CSF. Among the various hematopoitin receptor superfamily members, G-CSFr is most closely related to gp 130, the signal-transducing component of the IL-6, oncostatin M, and leukemia inhibitory factor receptors. Recent studies have demonstrated that in myeloid leukemia cell lines, G-CSF treatment results in rapid tyrosine phosphorylation of G-CSFr, JAK1 and JAK2 tyrosine kinases and the members of the STAT family of transcription factors.

S. E. Nicholson et al. 91 *Proc. Nat. Acad. Sci. USA* 2985 (1994) and S. S. Tian et. al., 84 *Blood* 1760 (1994).

Although many cytokines activate STAT proteins that can bind to similar sequences (GAS/APREs), they regulate distinct sets of genes. This suggests that there is specificity with respect to the response elements in some of these genes, such that they respond only to one of these cytokines. It is therefore possible that distinct classes of GAS-like sequences exist that are selective in their ability to respond to various cytokines. Accordingly, specific DNA sequences that show selectivity with respect to their ability to bind cytokine-activated proteins, including STAT proteins, would be useful tools allowing the responses mediated by different cytokine-activated DNA-binding proteins to be assayed selectively.

The disclosures of the above-cited references are hereby incorporated by reference in their entirety.

SUMMARY OF THE INVENTION

The present invention is directed to oligonucleotide sequences comprising DNA regulatory elements that bind, either directly or indirectly, to activated transcriptional regulatory proteins, preferably STAT proteins, in response to signaling molecules, including cytokines such as interferon gamma (IFNγ), interleukin 3 (IL-3), interleukin 4 (IL-4), interleukin 6 (IL-6), interleukin 13 (IL-1 3), erythropoietin (Epo), granulocyte colony stimulating factor (G-CSF) and granulocyte-macrophage colony stimulating factor (GM-CSF). Surprisingly, a spacing of 4, 5, 6 or 7 nucleotides between each half-site of the regulatory elements results in discrete regulatory elements that bind a variety of activated transcriptional regulatory proteins and/or specifically bind a single type or class of activated transcriptional regulatory protein. Accordingly, the regulatory elements of the present invention can be used in transcriptional assays to discover selective agonists or antagonists of a signaling molecule, such as IL-4, and its cognate transcriptional regulatory protein, STAT6.

In particular, the present invention provides an oligonucleotide sequence comprising a regulatory element of the nucleotide sequence TTN$_x$AA, wherein N is independently selected from the nucleotides A, T, C or G and x is 4, 5, 6 or 7 and wherein the regulatory element binds to an activated transcriptional regulatory protein in response to a signaling molecule. More preferably, the regulatory elements comprise nucleotide sequences selected from the group consisting of TTCN$_y$GAA, TTAN$_y$GAA, TTAN$_y$TAA, TTTN$_y$GAA and TTTN$_y$TAA, where N has the same meaning given above, and y is 2, 3, 4 or 5 (SEQ ID Nos 5–21). These oligonucleotide sequences can be double stranded, including their complements.

The present invention also provides a DNA construct comprising the oligonucleotide sequence described above operably linked to a promoter, which promoter is operably linked to a heterologous gene, wherein the DNA construct is linked in such a manner that the heterologous gene is under the transcriptional control of the oligonucleotide sequence and promoter. Also provided is a host cell transfected with this DNA construct.

The present invention also provides a method for the controlled expression of a heterologous gene of interest comprising culturing the transfected host cells containing an appropriate transcriptional regulatory protein(s) in the presence of a signaling molecule. Preferably, the signaling molecule in this method comprises a cytokine and the transcriptional regulatory protein comprises a STAT protein.

The present invention further provides a method for detecting the presence of a transcriptional regulatory protein, such as a novel STAT protein, in a sample comprising contacting the sample with an oligonucleotide sequence as described above under conditions where the transcriptional regulatory protein is activated and binds with the oligonucleotide sequence to form a complex, and detecting the presence of the complex in the sample. Thereafter, the complex can be separated from the sample, and the transcriptional regulatory protein isolated from the regulatory element.

Further, the present invention provides a method for measuring the ability of a compound to act as an agonist of gene transcription comprising (a) contacting the compound with a transfected host cell as described above under conditions in which the heterologous gene is capable of being expressed in response to the compound, and (b) comparing the level of gene expression in step (a) with the level of gene expression from the host cell in the absence of the compound. Alternatively, the present invention also provides a method for measuring the ability of a compound to act as an antagonist of gene transcription comprising (a) contacting the compound with a transfected host cell as described above in the presence of a predetermined amount of a signaling molecule under conditions in which the heterologous gene is capable of being expressed in response to the signaling molecule, and (b) comparing the level of gene expression in step (a) with the level of gene expression from the host cell in the presence of the signaling molecule, but the absence of the compound. In both these methods, the heterologous gene may be any appropriate reporter gene such as the heterologous gene for luciferase, chloramphenicol acetyl transferase, green fluorescent protein or β-galactosidase.

The present invention also provides an IL-4 and IL-13 selective oligonucleotide sequence comprising ANTTCNNNNGAANA (SEQ ID NO. 152) or its complement TNTTCNNNNGAANT (SEQ. ID NO. 153), wherein N is independently selected from A, T, C or G, and wherein the oligonucleotide sequence, when operably linked to a promoter and a heterologous gene, binds to an activated transcriptional regulatory protein comprising STAT6 protein activated by IL-4 and/or IL-13, and transcriptionally modulates the heterologous gene.

These and various other advantages and features of novelty which characterize the invention are pointed out with particularity in the claims annexed hereto and forming a part hereof However, for a better understanding of the invention, its advantages, and objects obtained by its use, reference should be had to the accompanying drawings and descriptive matter, in which there is illustrated and described preferred embodiments of the invention.

DEFINITIONS

For the purposes of this invention:

"Oligonucleotide" or "DNA" molecule or sequence refers to a molecule comprised of the deoxyribonucleotides adenine (A), guanine (G), thymine (T) and/or cytosine (C), in either single-stranded form or a double-stranded helix, and comprises or includes a "regulatory element" according to the present invention, as that term is defined herein. The exact size, strandedness and orientation (i.e. 3' to 5', or 5' to 3') will depend upon many factors, which, in turn, depend upon the ultimate function and use of the oligonucleotides of the present invention. Thus, the term "oligonucleotide" or "DNA" includes double-stranded DNA found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. "Regulatory element" refers to a deoxyribonucleotide sequence comprising the whole, or a portion of, an oligonucleotide sequence to which an activated transcriptional regulatory protein, or a complex comprising one or more activated transcriptional regulatory proteins, binds so as to transcriptionally modulate the expression of an associated gene or genes, including heterologous genes. "Signaling molecule" refers to an extracellular polypeptide, oligosaccharide or other non-peptidyl molecule, in either a free or bound form, that interacts with a receptor at or near the surface of a cell. This interaction in turn triggers an intracellular pathway which includes the activation of one or more transcriptional regulatory proteins that bind to a regulatory element, thereby transcriptionally modulating the expression of an associated gene or genes. As used herein, "signaling molecule" includes naturally occurring molecules, such as cytokines, peptidyl and non-peptidyl hormones, antibodies, cell-surface antigens, or synthetic mimics of any of these signaling molecules, or synthetic molecules that mimic the action of any of these signaling molecules. "Cytokines" refer to a diverse grouping of soluble polypeptides, including growth factors and hormones, that control the growth, differentiation and function of cells in such a manner as to ultimately elicit a phenotypic response in an organism. Preferred cytokines useful with the regulatory elements and associated methods of the present invention include IFNγ, IL-2, IL-3, IL-4, IL-5, IL-6, IL-7, IL-9, IL-10, IL-11, IL-12, IL-13, IL-15, GM-CSF, Epo, Tpo, growth hormone, prolactin, Oncostatin M, G-CSF, LIF, EGF, CNTF and PDGF. "Transcriptional regulatory protein" refers to cytoplasmic or nuclear proteins that, when activated, bind the regulatory elements/oligonucleotide sequences of the present invention either directly, or indirectly through a complex of transcriptional regulatory proteins or other adapter proteins, to transcriptionally modulate the activity of an associated gene or genes. Thus, transcriptional regulatory proteins can bind directly to the DNA regulatory elements of the present invention, or can bind indirectly to the regulatory elements by binding to another protein, which in turn binds to or is bound to a DNA regulatory element of the present invention. See e.g., S. A. Veals et al., 13 *Molec. Cell. Biol.,* 196–206 (1993). As used herein, transcription regulatory proteins, include, but are not limited to, those proteins referred to in the art as STAT proteins (Z. Zhong et al., 264 *Science,* 95) STF proteins (C. Schindler et al., 13 *EMBO J.,* 1350 (1994)), Mammary Gland-Specific Nuclear Factor (M. Schmidt-Ney et al., 6 *Mol. Endochronol.,* 1988 (1992) and H. Wakao et al., 267 *J. Biol. Chem.,* 16365 (1992)), APRF (Wegenka, 13 *Mol. Cell Bio.,* 276), GHIF (Mayer, 269 J. Biol. Chem., 4701), GHSF and EPOSF (Finbloom, 14 *Mol. Cell Bio.,* 2113), as well as to all substantially homologous analogs and allelic variations thereof.

"Transcriptionally modulate the expression of an associated gene or genes" means to change the rate of transcription of such gene or genes.

"STAT protein" refers to those transcriptional regulatory proteins designated as "Signal Transducers and Activators of Transcription" (STAT) by Dr. J. E. Darnell of Rockefeller University. See Zhong, 264 *Science* 95. As used herein, STAT proteins include the p91 (STAT1α), p84 (STAT1β), p113 (STAT2) proteins and the STAT-associated p48 family of proteins. S. A. Veals et al., 12 *Mol. Cell. Biol.,* 3315

(1992). Further, STAT proteins also include a binding protein designated as STAT3 (Zhong, 264 *Science* 95), and a binding protein designated as STAT4 (Id.). In addition, MGF is now renamed STAT5 (Gouilleux et al., 13 *EMBO J.*, 4361–4369 (1994)) and STAT-IL-4 (or STAT6) has recently been cloned. Hou et al., 265 *Science*, 730 (1994) and J. N. Ihle et al., 11 *Trends in Genetics*, 69 (1995). Also included are substantially homologous analogs and allelic variations of all of the above STAT proteins. "Activate", "activated", "activation" or derivatives thereof, means that one or more transcriptional regulatory proteins within a cell are modified post-translationally, or are constituitively active, such that they can bind directly or indirectly to DNA regulatory elements/oligonucleotide sequences of the present invention in a sequence-specific manner. This modification will typically comprise phosphorylation of the transcriptional regulatory proteins via a variety of mechanisms, including, but not limited to activation by various protein kinases. See, e.g., (Shuai, 258 *Science*, 1808 an P. Cohen, 17 *TIBS*, 408 (1992)).

"DNA construct" refers to any genetic element, including, but not limited to, plasmids, vectors, chromosomes and viruses, that incorporate the oligonucleotide sequences of the present invention. For example, the DNA construct can be a vector comprising a promoter that is operably linked to an oligonucleotide sequence of the present invention, which is in turn, operably linked to a heterologous gene, such as the gene for the luciferase reporter molecule.

"Promoter" refers to a DNA regulatory region capable of binding directly or indirectly to RNA polymerase in a cell and initiating transcription of a downstream (3' direction) coding sequence. For purposes of the present invention, the promoter is bounded at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Dalgarno sequences in addition to the −10 and −35 consensus sequences.

"Gene" refers to a nucleic acid molecule, the sequence of which includes all the information required for the normal regulated production of a particular protein. A "heterologous" region of a DNA construct (i.e. a heterologous gene) is an identifiable segment of DNA within a larger DNA construct that is not found in association with the other genetic components of the construct in nature. Thus, when the heterologous gene encodes a mammalian gene, the gene will usually be flanked by a promoter that does not flank the structural genomic DNA in the genome of the source organism.

A promoter of a DNA construct, including an oligonucleotide sequence according to the present invention, is "operably linked" to a heterologous gene when the presence of the promoter influences transcription from the heterologous gene, including genes for reporter sequences such as luciferase, chloramphenicol acetyl transferase, β-galactosidase, green fluorescent protein and secreted placental alkaline phosphatase. Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

A host cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mamrnmalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA.

"Host cell" refers to a cell line that expresses, either normally or after transfection of the requisite cDNAs, the relevant receptor components for a given signaling molecule, signaling (e.g., kinase) proteins, transcriptional regulatory proteins, and accessory factors such that, upon binding of the signaling molecule to the cell surface, transcriptional regulatory protein-mediated gene transcription is affected. Preferably, the host cell line is responsive to cytokines, such that the host cell line expresses, either normally or after transfection of the requisite cDNAs, the relevant cytokine receptor components, JAK proteins, STAT proteins, and accessory factors such that, upon cytokine binding to the cell surface, STAT-mediated gene transcription is affected.

BRIEF DESCRIPTION OF THE DRAWINGS

The invention may be further illustrated by reference to the accompanying Drawings wherein:

FIG. 1A depicts a general reporter construct that contains a regulatory element (single or multimerized) upstream of an operational promoter sequence, the two of which are operably linked to a downstream heterologous reporter gene sequence. FIG. 1B depicts the more specific reporter constructs used in the experiments described in the Examples herein and summarized in Tables 7–10 and 15–16. Thus, the reporter constructs used contain a (multimerized) regulatory element located upstream of the Herpes Simplex virus thymidine kinase −35 to +10 (with respect to the cap site) promoter sequence, the two of which are operably linked to a downstream firefly luciferase reporter gene sequence; and FIGS. 2A to 2D are reproductions of Electrophoretic Mobility Shift Assay (EMSA) autoradiograms that show the binding patterns of transcriptional regulatory protein-DNA binding complexes activated by IFNγ, IL-6, GM-CSF and IL-4. The EMSA's were performed as described in Example 1 herein. The radiolabeled, double-stranded oligonucleotide probes utilized in the EMSAs of FIGS. 2A–2D were made by annealing the oligonucleotides of SEQ ID NOs 66 and 67 (FIG. 2A), 76 and 77 (FIG. 2B), 78 and 79 (FIG. 2C) and 80 and 81 (FIG. 2D).

DETAILED DESCRIPTION OF EMBODIMENTS OF THE INVENTION

Figure 1A:
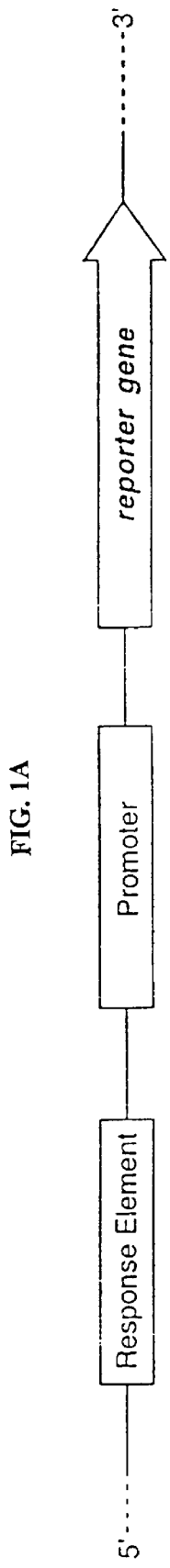
FIGS. 1A and 1B are schematic depictions of the reporter constructs that can be used to assess the transcriptional activity of transcriptional regulatory proteins that bind to the regulatory elements/oligonucleotide sequences of the present invention.

The present inventors have discovered a series of DNA regulatory elements (i.e. response elements) that in response to various signaling molecules, bind, either directly or indirectly, to activated transcriptional regulatory proteins, and accordingly, transcriptionally modulate the expression of one or more genes operably linked with such regulatory elements. In this regard, the inventors have surprisingly discovered that a change in the spacing of 4, 5, 6 or 7 nucleotides within the regulatory elements can transform an element from one that binds with a variety of cytokine-induced, activated transcriptional regulatory proteins to a regulatory element that selectively binds just one type or class of cytokine-induced, activated transcriptional regulatory proteins. For example, in the sequence $TTN_xAA$, a spacing of four spacer nucleotides (i.e. x=4) results in a regulatory element that is selective for an activated STAT3 transcriptional regulatory protein (e.g., induced by IL-6, IL-10, IL-11, LIF, EGF, PDGF or G-CSF), while a spacing of six or seven spacer nucleotides yields a regulatory element that is selective for the activated transcriptional regulatory protein(s) induced by the IL-4, IL-7, IL-9, IL-13 and IL-15 cytokines. However, utilization of five spacer nucleotides results in a regulatory element that binds a variety of different cytokine-induced transcriptional regulatory proteins, including the STAT1α and STAT3 proteins, as well as those transcriptional regulatory protein(s) that are induced by the IL-2, IL-3, IL-4, IL-5, IL-7, IL-9, IL-10, IL-11, IL-12, IL-13, IL-15, Epo, Tpo, growth hormone, prolactin, G-CSF and GM-CSF cytokines (e.g., STAT5 and/or STAT6).

The regulatory elements according to the present invention are selected from the nucleotide sequence $TTN_xAA$, wherein N is a spacer nucleotide independently selected from A, T, C or G and x is 4, 5, 6 or 7. More preferably, the regulatory elements comprise nucleotide sequences selected from the group consisting of $TTCN_yGAA$, $TTAN_yGAA$, $TTAN_yTAA$, $TTTN_yGAA$ and $TTTN_yTAA$, where N has the same meaning given above, and y is 2, 3, 4 or 5 (SEQ ID NOs 5–21). The preferred nucleotide sequences according to the present invention include:

| | |
|---|---|
| TTNNNNAA (SEQ ID NO: 1) | TTNNNNNAA (SEQ ID NO: 2) |
| TTNNNNNNAA (SEQ ID NO: 3) | TTNNNNNNNAA (SEQ ID NO: 4) |
| TTCNNGAA (SEQ ID NO: 5) | TTCNNNGAA (SEQ ID NO: 6) |
| TTCNNNNGAA (SEQ ID NO: 7) | TTANNGAA (SEQ ID NO: 8) |
| TTANNNGAA (SEQ ID NO: 9) | TTANNNNGAA (SEQ ID NO: 10) |
| TTANNNNNGAA (SEQ ID NO: 11) | TTANNNTTA (SEQ ID NO: 12) |
| | TTANNNNNTAA (SEQ ID NO: 14) |
| TTANNNNTAA (SEQ ID NO: 13) | TTTNNNGAA (SEQ ID NO. 16) |
| TTTNNGAA (SEQ ID NO: 15) | TTTNNNNNGAA (SEQ ID NO. 18), |
| TTTNNNNGAA (SEQ ID NO. 17) | TTTNNNNTAA (SEQ ID NO. 20), |
| TTTNNNTAA (SEQ ID NO. 19) | and |
| TTTNNNNNTAA (SEQ ID NO. 21) | | where each N is independently selected from A, T, C, or G.

Especially preferred regulatory element sequences according to the present invention include: TTCCCGAA (SEQ ID NO.22), TTCCCCGAA (SEQ ID NO.23), TTCCCCCGAA (SEQ ID NO.24), TTCCGGAA (SEQ ID NO. 25), TTCCCGGAA (SEQ ID NO.26), TTCCCCGGAA (SEQ ID NO.27), TTCCTGGAA (SEQ ID NO.28), TTCCTTGGAA (SEQ ID NO.29), TTCCAGAA (SEQ ID NO.30), TTCCCAGAA (SEQ ID NO. 31), TTCCCCAGAA (SEQ ID NO. 32), TTCTTTGAA (SEQ ID NO. 33), TTCTTTTGAA (SEQ ID NO.34), TTCTCAGAA (SEQ ID NO. 35), TTCTCCAGAA (SEQ ID NO. 36), TTACCGTAA (SEQ ID NO. 37), TTACCCGTAA (SEQ ID NO.38), TTACCCCGTAA (SEQ ID NO.39), TTCCCGTAA (SEQ ID NO. 40), TTCCCCGTAA (SEQ ID NO. 41), TTCCCCGTAA (SEQ ID NO. 42), TTCTGTAA (SEQ ID NO. 43), TTCTCGTAA (SEQ ID NO. 44), TTCTCCGTAA (SEQ ID NO. 45), TTCTCCCGTAA (SEQ ID NO. 46), TTCCAAGAA (SEQ ID NO. 47), TTTCCCGTAA (SEQ ID NO. 48), TTCCCAGGAA (SEQ ID NO. 49), TTCTTAAGAA (SEQ ID NO. 50), TTCTAAGAA (SEQ ID NO. 51), TTTCCCCGAA (SEQ ID NO. 52), TTTCTAAGAA (SEQ ID NO. 53).

In this regard, the regulatory elements of SEQ ID NOs 22, 25, 30 and 43 comprise STAT3 protein selective regulatory elements, SEQ ID NOs 37, 40 and 44 comprise STAT1α and STAT3 selective regulatory elements, SEQ ID NOs 23, 26, 28, 31, 51, 52 and 53 comprise regulatory elements that bind a variety of activated transcriptional regulatory proteins, SEQ ID NOs 33, 35, 38, 41 and 45 comprise regulatory elements that bind GM-CSF, IL-2 and IL-4 activated transcriptional regulatory proteins, and SEQ ID NOs 24, 27, 29, 32, 34, 36, 39, 42, 46, 47, 48, 49 and 50 comprise regulatory elements that selectively bind activated transcriptional regulatory protein(s) induced by IL-4 and IL-13. Furthermore, these regulatory elements alone, or with additional flanking nucleotide sequences, form the oligonucleotide sequences according to the present invention. In this regard, it is preferable that such oligonucleotide sequences comprise between 8 and 200 nucleotides, including the regulatory elements of the present invention. However, sequences in excess of 200 nucleotides that contain the regulatory elements of the present invention, that are capable of binding activated transcriptional regulatory proteins, and of transcriptionally modulating the expression of one or more genes thereby, are also considered to be within the scope of the present invention. In this regard, it will be understood by those skilled in the art that, while the observed spacing preferences are an important determinant of selective binding and transcriptional activity, the particular sequences of the spacer nucleotides as well as the particular sequences of the nucleotides flanking the core elements also influence binding and transactivation.

The oligonucleotide sequences of the present invention can also comprise multimers of two or more "units" of the basic regulatory elements. In this regard, such multimer oligonucleotide sequences can, as a practical matter, contain from about 2 to 15 units of the same or different regulatory elements according to the present invention. However, theoretically, there is no limit to the number of regulatory elements within such a multimer oligonucleotide sequence. Such multimeric oligonucleotide sequences are useful as probes for detecting, isolating and/or purifying transcriptional regulatory proteins. Further, when used in a DNA construct, including a promoter and heterologous gene, according to the present invention, a multimer of the regulatory elements can enhance the expression of the gene from the DNA construct in response to various cytokines or other signaling molecules.

A variety of signaling molecules activate transcriptional regulatory proteins that bind directly or indirectly to the regulatory elements/oligonucleotide sequences of the present invention. Nonlimiting examples of such signaling molecules include polypeptides such as cytokines and antibodies, and cell-surface antigens, oligosaccharides typically found at or near the surface of cell, non-peptidyl molecules such as TUBag4 (P. Constant et al., 264 *Science*, 267 (1994)) and synthetic mimics of any of these molecules, in both their free and bound forms. Thus, the present invention includes cell to cell or cell to substrate transcriptional regulatory protein activation via signaling molecules bound to or near the surface of a cell or other substrate.

Preferably, the signaling molecules according to the present invention comprise cytokines that activate transcriptional regulatory proteins that bind to the regulatory elements/oligonucleotide sequences of the present invention. Examples of such cytokines include, but are not limited to, Interleukins 2, 3, 4, 5, 6, 7, 9, 10, 11, 12, 13 and 15 (IL-2, IL-3, IL-4, IL-5, IL-6, IL-7, IL-9, IL-10, IL-11, IL-12, 15), granulocyte-macrophage colony stimulating factor (GM-CSF), granuloctyte colony stimulating factor (G-CSF), colony stimulating factor 1 (CSF-1), interferons alpha, beta, and gamma (IFNα, IFNβ, IFNγ), epidermal growth factor (EGF), platelet-derived growth factor (PDGF), leukemia inhibitory factor (LIF), Oncostatin M, nerve growth factor (NGF), ciliary neurotrophic factor (CNTF), brain-derived neurotrophic factor (BDNF), erythropoietin (Epo), thrombopoietin (Tpo), growth hormone and prolactin. Particularly preferred cytokines according to the present invention include, but are not limited to, IFNα, IFNγ, IL-2, IL-3, IL-4, IL-5, IL-6, IL-7, IL-9, IL-10, IL-11, IL-12, IL-13, IL-15, G-CSF, GM-CSF, Epo, Tpo, Oncostatin M, G-CSF, LIF, EGF, PDGF and CNTF.

The regulatory elements and/or oligonucleotide sequences of the present invention will also prove useful in detecting, isolating and purifying new transcriptional regulatory proteins that display binding specificity to the regulatory elements/oligonucleotide sequences of the present invention. Further, it is contemplated that these regulatory elements/oligonucleotide sequences will prove particularly useful in the discovery of novel STAT proteins or STAT-related transcriptional regulatory proteins. In this regard, detection of such novel transcriptional regulatory proteins can be accomplished with the following technique. Cells, such as HepG2 cells, are treated with an appropriate cytokine, for example, with IFNγ for 15 minutes to induce the activation of one or more transcriptional regulatory proteins. Extracts of the nucleus and cytoplasm of these cells are then prepared using conventional methods and tested for binding to the regulatory elements/oligonucleotide sequences by an electrophoretic mobility shift assay, in comparison with untreated cells that will show little or no specific binding as described in Levy, 3 *Genes Dev.,* 1362 and Kessler, 4 *Genes Dev.,* 1753, the disclosures of which are herein incorporated by reference. Furthermore, DNA regulatory element binding activity may also be stimulated in vitro by treating a cytoplasmic extract, supplemented with cell membranes, with a signaling molecule, such as a cytokine.

If an antibody specific for a transcriptional regulatory protein is available, it can be used to specifically interfere with the binding of the regulatory element of the present invention to the activated transcriptional regulatory protein, thereby assisting in the identification of the transcriptional regulatory protein. Furthermore, an unknown transcriptional regulatory protein identified or purified using the regulatory elements/oligonucleotide sequences of the present invention can be used to immunize animals to prepare an antibody specific for the transcriptional regulatory protein using methods well known in the art. See, e.g., E. Harlow, et al., Antibodies: A Laboratory Manual, Cold Spring Harbor Laboratory Press, Cold Spring Harbor, N.Y. (1988), the disclosure of which is herein incorporated by reference.

Thus, the regulatory elements/nucleotide sequences of the present invention thus can serve as a "probe", similar to those used in a variety of nucleic acid detection systems well known in the art, except that the probes of the present invention are used to detect proteins, rather than a nucleic acid sequences, which specifically bind to the regulatory elements/oligonucleotide sequences of the present invention.

The sensitivity of such a nucleic acid detection assay can be increased by altering the manner in which a signal is detected by an observer. For example, assay sensitivity can be increased through the use of labeled oligonucleotide sequences using a wide variety of detectable labels, including, without limitation, enzyme labels, radioisotopic labels, fluorescent labels, and modified bases. See, e.g., U.S. Pat. Nos. 4,581,333, 4,358,535, 4,446,237, 4,582,789, and 4,563,417, as well as European Patent Application Nos. EP 144914 and EP 119448, the disclosures of which are herein incorporated by reference. Thus, DNA probes according to the present invention preferably include the regulatory elements alone, or as part of a longer oligonucleotide sequence of the present invention, labeled with a detectable label, such as a radioisotope, an enzyme, a fluorescent label, a chemical label, or a modified base.

Thus, the present invention provides a method for detecting the presence of novel transcriptional regulatory proteins in a sample. Such samples are preferably biological samples, including, but not limited to, cells, cell culture supernatant, cell or tissue extracts, or particular fractions thereof, and other biological fluids such as blood, sera, urine, saliva, etc. Binding of the probe containing the regulatory elements/oligonucleotide sequences of the present invention to a transcriptional regulatory protein in the sample may be detected by any appropriate means known in the art. For example, direct or indirect, or competitive binding assays may be used. In such assays, association of the labeled probe with the proteinaceous material of the sample is then detected. In a preferred embodiment, the oligonucleotide sequence is modified by the incorporation of a radioactively labeled nucleotide.

Once detected, the novel transcriptional regulatory protein can be separated and purified from the probe-protein complex by any of a variety of techniques well known to those of skill in the art. For example, such isolation and purification can be based on affinity chromatography, which relies on the interaction of the protein to be purified with an immobilized ligand. In the present invention, a regulatory element and/or oligonucleotide sequence of the present invention immobilized on a support would serve as the immobilized ligand, which in turn would be used to isolate and purify a novel transcriptional regulatory protein from a sample.

In a preferred embodiment, the regulatory element/oligonucleotide sequence of the present invention is immobilized on a solid support or carrier. As used herein "solid phase carrier or support" refers to any support capable of binding the oligonucleotide sequences/DNA regulatory elements of the present invention. Well known supports, or carriers, include glass, polystyrene, polypropylene, polyethylene, dextran, nylon, amyloses, natural and modified celluloses, polyacrylamides, agaroses, and magnetite. Methods for coupling nucleic acids to the solid phase, the solid phase substances useful in these methods, and the means for elution of the proteins from the bound ligand, are well known to those of skill in the art.

In addition to the specific methods described above, purification steps prior to affinity separation may also include one or more additional methods, such as ammonium sulfate precipitation, size exclusion chromatography (gel filtration), ion exchange chromatography, differential precipitation and the like, all well known in the art. Also useful is the method known as hydrophobic interaction chromatography (HIC) which is based on the interaction between the solute and the gel that is hydrophobic. Hydrophobic interactions are strongest at high ionic strength, therefore, this form of separation is conveniently performed following salt precipitations or ion exchange procedures. Elution from HIC supports can be effected by alterations in solvent, pH, ionic strength, or by the addition of chaotropic agents or organic modifiers, such as ethylene glycol. General principles of HIC are described in U.S. Pat. Nos. 3,917,527 and 4,000,098. Purification of specific proteins using HIC is described in the U.S. Pat. Nos. 4,332,717; 4,771, 128; 4,743,680; 4,894,439; 4,908,434; and 4,920,196, the disclosures of which are herein incorporated by reference.

The regulatory elements/oligonucleotide sequences of the present invention may be included in a recombinant DNA construct which contains a regulatory element/oligonucleotide sequence operably linked to a promoter and a heterologous gene. Typically the heterologous gene comprises a reporter sequence, such as the gene for luciferase. In this regard, a recombinant DNA construct, such as a reporter plasmid according to the present invention, can be constructed using conventional molecular biology, microbiology, and recombinant DNA techniques well known to those of skill in the art. Such techniques are explained fully in the literature, including Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins, eds. (1984)]; "Animal Cell Culture" [R. I. Freshney, ed. (1986)], "Immobilized Cells and Enzymes" [IRL Press, (1986)] and B. Perbal, "A Practical Guide to Molecular Cloning" (1984), the disclosures of which are herein incorporated by reference.

Promoter sequences useful in DNA constructs according to the present invention include all prokaryotic, eukaryotic or viral promoters capable of driving transcription of a heterologous gene of interest in combination with a regulatory element of the present invention, when transfected into an appropriate host cell. Suitable prokaryotic promoters include, but are not limited to, promoters recognized by the T4, T3, Sp6, and T7 polymerases, the $P_R$ and $P_L$ promoters of bacteriophage , the transcriptional regulatory protein, recA, heat shock, and lacZ promoters of *E. coli*, the -amylase and the −28-specific promoters of *B. subtilis,* the promoters of the bacteriophages of *Bacillus, Streptomyces* promoters, the int promoter of bacteriophage, the bla promoter of the β-lactamase gene of pBR322 and the CAT promoter of the chloramphenicol acetyl transferase gene of pPR325. See, e.g., B. R. Glick, 1 *J. Ind. Microbiol.,* 277–282 (1987); Y. Cenatiempo, 68 *Biochimie,* 505–516 (1986); J. D. Watson et al., In: *Molecular Biology of the Gene,* Fourth Edition, Benjamin Cummins, Melno Park, Calif. (1987) and S. Gottesman, 18 *Ann. Rev. Genet.,* 415–442 (1984), the disclosures of which are herein incorporated by reference. Preferred eukaryotic promoters include the yeast cyc-1promoter, the promoter of the mouse metallothionein I gene, the thymidine kinase promoter of the Herpes simplex virus, the SV40 early promoter, and the yeast gal-4 gene promoter. See Guarante et al., 78 *Proc. Natl. Acad. Sci. USA,* 2199–2203 (1981), D. Hamer et al., 1 *J. Mol. Appl. Gen.,* 273–288 (1982), S. McKnight, 31 *Cell,* 355–365 (1982), C. Benoist et al., 290 *Nature (London),* 304–310 (1981), S. A. Johnston et al., 79 *Proc Natl. Acad. Sci. (USA),* 6971–6975 (1982) and P. A. Silver et al., 81 *Proc. Natl. Acad. Sci. (USA),* 5951–5955 (1984), the disclosures of which are herein incorporated by reference herein. Preferably, a DNA construct according to the present invention utilizes the thymidine kinase gene promoter of the Herpes simplex virus.

The third component of the recombinant DNA or construct molecules of the present invention is a "heterologous gene" which may be composed of any set of nucleotides regardless of sequence. Nonlimiting examples of such heterologous genes include the structural genes for luciferase, β-galactosidase, chloramphenicol acetyl transferase, secreted placental alkaline phosphatase, human growth hormone, tPA, green fluorescent protein and interferon. For a more extensive list of heterologous genes usable in the constructs and methods of the present invention, see Beaudet, 37 *Am. J. Hum. Gen.,* 386–406 (1985).

Preferably the heterologous gene comprises a reporter gene whose product is used to assess regulation of transcription via a promoter and a regulatory element/oligonucleotide sequence of the present invention. The expression of this "reporter sequence" results in the formation of a reporter product (e.g., protein) which is readily detectable. The reporter sequence will preferably be selected such that the reporter molecule will have a physical and chemical characteristics which will permit or facilitate its identification or detection by means well known in the art. In one embodiment, the presence of the reporter molecule will be detected through the use of an antibody or an antibody fragment, capable of specific binding to the reporter molecule. In another embodiment, a reporter such as β-galactosidase or luciferase can be assayed enzymatically or immunologically.

A preferred reporter molecule is LUC, well known in the art. See, e.g., J. R. De-Wet et al., 7 *Mol. Cell Bio.,* 725 (1987). Because this is an insect gene, it is absent from mammalian cells and the enzyme product can be directly assayed in a cell extract. The level of enzyme activity corresponds to the amount of enzyme that was made, which in turn reveals the level of expression. In addition, LUC mRNA may also be measured directly.

Typically, a plasmid containing the recombinant DNA molecule of the present invention, including the LUC gene, is introduced into mammalian cells, which are then grown to, at or near confluency. In this regard, any host cell capable of activating one or more transcriptional regulatory proteins in response to an appropriate signaling molecule or molecules can be transfected with the DNA constructs of the present invention. Preferably, such cytokine-responsive host cells comprise mammalian cells, such as HepG2, U937, ME-180, TF-1 and NFS-60 cells.

The reporter cells are treated with a compound or sample suspected of containing a signaling molecule capable of inducing or activating a transcriptional regulatory protein, for example, a sample of growth medium that has been in contact with cells and may contain signaling molecules secreted or released by the cells. The LUC-producing reporter cells are extracted, and the soluble extracts are supplemented with luciferin and ATP. In the presence of these compounds the action of luciferase generates light, which is detected using a luminometer. The amount of light produced is directly related to the amount of luciferase present in the cellular extract.

With a suitable DNA construct transfected into a host cell, the present invention provides a method for the controlled expression of a gene of interest. Thus, application of a signaling molecule, such as cytokine, to transfected host cells can be used to drive the expression of a heterologous gene to yield defined quantities of a desired product, such as human growth hormone, by any of a variety of cell culture and fermentation techniques well known to those of skill in the art.

Alternatively, when the DNA construct comprises a reporter sequence, such as the gene for luciferase, transfection of the DNA construct into a host cell provides a convenient means for measuring the transcriptional activity of a reporter product in response to a signaling molecule, such as a cytokine or a sample of growth medium that has been in contact with cells and may contain signaling molecules secreted or released by the cells.

Importantly, when transcription of LUC is activated by the transcriptional regulatory protein being assayed, LUC synthesis is increased relative to a control lacking the transcriptional regulatory protein. Thus, the amount of LUC enzyme produced is an indirect measure of transcription induced by the activated transcriptional regulatory protein binding to the regulatory elements/oligonucleotide sequences of the present invention, which is operably linked to the LUC gene.

When a preferred host cell, such as a HepG2 cell, is transfected with a reporter DNA construct according to the present invention, it can be utilized in assays to detect agonists and antagonists of signaling molecules that induce gene transcription via activated transcriptional regulatory proteins. As used herein, agonists or antagonists of gene transcription include compounds that intervene at any point within the signaling pathway from interaction between the signaling molecule and a cell surface receptor through activation of one or more transcriptional regulatory proteins and binding of the same to DNA regulatory elements, the end result of which is modulation of gene transcription. Further, as used herein, agonists and antagonists of gene transcription also include potentiators of known compounds with such agonist or antagonist properties. Agonists can be detected by contacting the transfected host cell with a compound or mix of compounds and, after a fixed period of time, determining the level of gene expression (e.g., the level of luciferase produced) within the treated cells. This expression level can then be compared to the expression level of the reporter gene in the absence of the compound(s). The difference between the levels of gene expression, if any, indicated whether the compound(s) of interest agonize the activation of intracellular transcriptional regulatory proteins in an analogous fashion to a known agonist signaling molecule, such as a cytokine. Further, the magnitude of the level of reporter product expressed between the treated and untreated cells provides a relative indication of the strength of that compound(s) as an agonist of gene transcription via a transcriptional regulatory protein pathway.

Alternatively, such a transfected host cell can be used to find antagonists of known agonists, e.g., cytokines such as IL-4, of gene transcription utilizing host cells transfected with the DNA constructs according to the present invention. In such an assay, the compound or compounds of interest are contacted with the host cell in conjunction with one or more known agonists (e.g., cytokines) held at a fixed concentration. The extent to which the compound(s) depress the level of gene expression in the host cell below that available from the host cell in the absence of compounds, but presence of the known agonist, provides an indication and relative strength of the antagonist properties of such compound(s).

Thus, the present invention provides methods to assay for agonists and antagonists of gene transcription utilizing the regulatory elements/oligonucleotides of the present invention in appropriate DNA constructs and transfected host cells. Further, the agonist and antagonist compounds discovered utilizing these methods can serve as pharmaceutical agents in the intervention of various cytokine-induced disease states and conditions, or to ameliorate disease states caused by cytokine deficiency, such as inflammation, infection, anemia, cytopenia and cancerous or precancerous conditions.

The invention will be further illustrated by reference to the following non-limiting Examples.

EXAMPLE 1

Reagents

Oligonucleotides were obtained from Operon Technologies (Alameda, Calif.). IFNγ was the gift of Dr. J. E. Darnell (Rockefeller University, New York, N.Y.: commercially available from Genzyme, Cambridge, Mass.). Recombinant human IL-6, GM-CSF, Oncostatin M, IL-3 and IL-4 were obtained from R&D Systems (Minneapolis, Minn.). Recombinant IL-13 was obtained from Biosource (Camarillo, Calif.). Recombinant IL-2 was obtained from Chiron (Emeryville, Calif.). Recombinant human Epo and G-CSF were from Amgen, Inc. (Thousand Oaks, Calif.). Protease inhibitors and poly d(I-C) poly d(I-C) were from Boehringer Mannheim (Indianapolis, Ind.).

Cells and cell culture HepG2 cells were obtained from ATCC (Rockville, Md.) and grown in Eagle's Minimum Essential Medium (EMEM, BioWhittaker, Walkersville, Md.) supplemented with fetal bovine serum (10% v/v), glutamine (2 mM) and gentamicin sulfate (50 µg/mL, BioWhittaker). U937 cells were obtained from Dr. J. E. Darnell (commercially available from ATCC) and grown in RPMI-1640 (BioWhittaker) supplemented with fetal bovine serum (10% v/v), glutamine (2 mM) and gentamicin sulfate (50 µg/mL). ME-180 cells were obtained from the ATCC and grown in McCoy's 5A (Gibco/BRL, Gaithersburg, Md.) supplemented with fetal bovine serum (10% v/v), glutamine (2 mM) and gentamicin sulfate (50 µg/mL). CTLL-2 and TF-1 cells were obtained from the ATCC and grown in RPMI-1640 (BioWhittaker) supplemented with fetal bovine serum (10% v/v), glutamine (2 mM), gentamicin sulfate (50 µg/mL), and IL-2 (CTLL-2, 200 U/mL) or GM-CSF (TF-1, 5 ng/mL). IL-3-dependent NFS-60 cells were obtained from Dr. J. N. Ihle (St. Jude Children's Research Hospital, Memphis, Tenn.) and were maintained in RPMI-1640 supplemented with fetal bovine serum (10% v/v), glutamine (2 mM), gentarnicin sulfate (50 µg/mL) and 10% WEHI-3B-conditioned growth medium (to provide IL-3). Factor-independent NFS-60 cells were selected by withdrawing WEHI-3B-conditioned medium from the culture medium. In about two weeks, the cells adjusted to the new growth conditions and proliferated as well as the parental NFS-60 cells. HepG2 and ME-180 cells were treated with cytokines at 50–75% confluency, U937, CTLL-2, TF-1, and NFS-60 cells at a density of $2 \times 10^5 - 1 \times 10^6$/ml. Cytokines were used at the following concentrations: IFNγ, 5 ng/ml, IL-4, 10–30 ng/ml, IL-6, 10 ng/ml, GM-CSF, 5 ng/ml, Epo, 4–6 U/mL, IL-2, 200 U/mL, IL-3, 20 ng/mL, IL-13, 60 ng/mL, and G-CSF, 20 ng/mL.

Preparation of Nuclear Extracts and Electrophoretic Mobility Shift Assays

Nuclear extracts were prepared by NP40 lysis as described in H. B. Sadowski and M. Z. Gilman, 362 Nature 79 (1993), the disclosure of which is herein incorporated by reference. Protein concentrations were measured using Bradford dye binding assay (Bio-Rad Laboratories, Hercules, Calif.). Nuclear extracts were prepared either from untreated HepG2 cells, HepG2 cells treated for 15 min with IFNγ, HepG2 cells treated for 15 min with IL-6, untreated U937 cells, U937 cells treated for 30 min with GM-CSF or IL-4, CTLL-2 cells starved of IL-2 for 18 h and then either left untreated or treated for 30 min with IL-2; TF-1 cells starved of GM-CSF for 18 h and then either left untreated or treated for 30 min with Epo, IL-3 or GM-CSF; ME-180 cells either left untreated or treated for 30 min with IL-4 or IL-13; and NFS-60 cells starved of IL-3 for 16–18 h then either left untreated or treated for 10 min with G-CSF, IL-3 or IL-6. The double-stranded probe oligonucleotides used in the Electrophoretic Mobility Shift Assays (EMSAS) were formed by annealing oligonucleotides with the sequences:

| | | |
|---|---|---|
| 5'-GATCTGCTTCCGAACGT | -3' | (SEQ ID NO. 54) |
| 3'- ACGAAGGCTTGCACTAG | -5' | (SEQ ID NO. 55) |
| 5'-GATCTGCTTCCCGAACGT | -3' | (SEQ ID NO. 56) |
| 3'- ACGAAGGGCTTGCACTAG | -5' | (SEQ ID NO. 57) |
| 5'-GATCTGCTTCCCCGAACGT | -3' | (SEQ ID NO. 58) |
| 3'- ACGAAGGGGCTTGCACTAG | -5' | (SEQ ID NO. 59) |
| 5'-GATCTGCTTCCCCCGAACGT | -3' | (SEQ ID NO. 60) |
| 3'- ACGAAGGGGGCTTGCACTAG | -5' | (SEQ ID NO. 61) |
| 5'-GATCTGCTTCCCCCCGAACGT | -3' | (SEQ ID NO. 62) |
| 3'- ACGAAGGGGGGCTTGCACTAG | -5' | (SEQ ID NO. 63) |
| 5'-GATCTGCTTCCCCCCCGAACGT | -3' | (SEQ ID NO. 64) |
| 3'- ACGAAGGGGGGGCTTGCACTAG | -5' | (SEQ ID NO. 65) |
| 5'-GATCTGCTTCCGGAACGT | -3' | (SEQ ID NO. 66) |
| 3'- ACGAAGGCCTTGCACTAG | -5' | (SEQ ID NO. 67) |
| 5'-GATCTGCTTCCCGGAACGT | -3' | (SEQ ID NO. 68) |
| 3'- ACGAAGGGCCTTGCACTAG | -5' | (SEQ ID NO. 69) |
| 5'-GATCTGCTTCCCCGGAACGT | -3' | (SEQ ID NO. 70) |
| 3'- ACGAAGGGGCCTTGCACTAG | -5' | (SEQ ID NO. 71) |
| 5'-GATCTGCTTCCCCCGGAACGT | -3' | (SEQ ID NO. 72) |
| 3'- ACGAAGGGGGCCTTGCACTAG | -5' | (SEQ ID NO. 73) |
| 5'-GATCTGCTTCCCCCCGGAACGT | -3' | (SEQ ID NO. 74) |
| 3'- ACGAAGGGGGGCCTTGCACTAG | -5' | (SEQ ID NO. 75) |
| 5'-GATCTGCTTCCTGGAACGT | -3' | (SEQ ID NO. 76) |
| 3'- ACGAAGGACCTTGCACTAG | -5' | (SEQ ID NO. 77) |
| 5'-GATCTGCTTCCTTGGAACGT | -3' | (SEQ ID NO. 78) |
| 3'- ACGAAGGAACCTTGCACTAG | -5' | (SEQ ID NO. 79) |
| 5'-GATCTGCTTCCTTTGGAACGT | -3' | (SEQ ID NO. 80) |
| 3'- ACGAAGGAAACCTTGCACTAG | -5' | (SEQ ID NO. 81) |
| 5'-GATCTGCTTCCAGAACGT | -3' | (SEQ ID NO. 82) |
| 3'- ACGAAGGTCTTGCACTAG | -5' | (SEQ ID NO. 83) |
| 5'-GATCTGCTTCCCAGAACGT | -3' | (SEQ ID NO. 84) |
| 3'- ACGAAGGGTCTTGCACTAG | -5' | (SEQ ID NO. 85) |
| 5'-GATCTGCTTCCCCAGAACGT | -3' | (SEQ ID NO. 86) |
| 3'- ACGAAGGGGTCTTGCACTAG | -5' | (SEQ ID NO. 87) |
| 5'-GATCTGCTTCCCCCAGAACGT | -3' | (SEQ ID NO. 88) |
| 3'- ACGAAGGGGGTCTTGCACTAG | -5' | (SEQ ID NO. 89) |
| 5'-GATCTGCTTCTTGAACGT | -3' | (SEQ ID NO. 90) |
| 3'- ACGAAGAACTTGCACTAG | -5' | (SEQ ID NO. 91) |
| 5'-GATCTGCTTCTTTGAACGT | -3' | (SEQ ID NO. 92) |
| 3'- ACGAAGAAACTTGCACTAG | -5' | (SEQ ID NO. 93) |
| 5'-GATCTGCTTCTTTTGAACGT | -3' | (SEQ ID NO. 94) |
| 3'- ACGAAGAAAACTTGCACTAG | -5' | (SEQ ID NO. 95) |
| 5'-GATCTGCTTCTTTTTGAACGT | -3' | (SEQ ID NO. 96) |
| 3'- ACGAAGAAAAACTTGCACTAG | -5' | (SEQ ID NO. 97) |
| 5'-GATCTGCTTCTAGAACGT | -3' | (SEQ ID NO. 98) |
| 3'- ACGAAGATCTTGCACTAG | -5' | (SEQ ID NO. 99) |
| 5'-GATCTGCTTCTCAGAACGT | -3' | (SEQ ID NO. 100) |
| 3'- ACGAAGAGTCTTGCACTAG | -5' | (SEQ ID NO. 101) |
| 5'-GATCTGCTTCTCCAGAACGT | -3' | (SEQ ID NO. 102) |
| 3'- ACGAAGAGGTCTTGCACTAG | -5' | (SEQ ID NO. 103) |
| 5'-GATCTGCTTCTCCCAGAACGT | -3' | (SEQ ID NO. 104) |
| 3'- ACGAAGAGGGTCTTGCACTAG | -5' | (SEQ ID NO. 105) |
| 5'-GATCGATTTCCCCGAAATG | -3' | (SEQ ID NO. 106) |
| 3'- CTAAAGGGGCTTTACCTAG | -5' | (SEQ ID NO. 107) |
| 5'-GATCCAATTTCTAAGAAAGGA | -3' | (SEQ ID NO. 108) |
| 3'- GTTAAAGATTCTTTCCTCTAG | -5' | (SEQ ID NO. 109) |
| 5'-GATCCACTTCCCAAGAACAGA | -3' | (SEQ ID NO. 110) |
| 3'- GTGAAGGGTTCTTGTCTCTAG | -5' | (SEQ ID NO. 111) | where the nucleotide sequences shown in bold type face correspond to nucleotide sequences, including their double-stranded complement, tested for activity as regulatory elements according to the present invention.

The annealed oligonucleotides were labeled by filling in the overhanging ends with Klenow fragment (Boehringer Mannheim) in the presence of [$\alpha$-$^{32}$P]-dGTP and/or [$\alpha$-$^{32}$P]-dATP (Amersham Corporation, Arlington Heights, Ill.). Electrophoretic mobility shift assays (EMSA's) were performed in HEPES buffer (13 mM, pH 7.6, Sigma Chemical, St. Louis, Mo.), containing sodium chloride (80 mM), sodium fluoride (3 mM), sodium molybdate (3 mM), DTT (1 mM), EDTA (0.15 mM), EGTA (0.15 mM), glycerol (8% v/v, including contributions from the nuclear extract), poly d(I-C) poly d(I-C) (75 µg/mL), radiolabeled probe (approximately 0.2ng) and nuclear extract containing 5–10 µg of total protein. Reactions were incubated at room temperature for 20 minutes then resolved on 5% polyacrylamide gels containing 0.25× TBE [1× TBE is Tris borate (89 mM), pH 8.0 containing EDTA (1 mM)] and glycerol (5% v/v). Gels were run at 4° C. in 0.25× TBE at 20V/cm, then dried and autoradiographed.

Relative binding affinities, as determined from the EMSA results for oligonucleotide SEQ ID NOs 54–105, were visually rated and assigned according to the following scale:

(–) band corresponding to specific complex on the EMSA autoradiogram (See e.g., FIG. 2C, lanes 2 and 3) barely discernible or not discernible.

(+) band corresponding to specific complex on the EMSA autoradiogram (See e.g., FIG. 2A, lane 3) easily discernible but of weak intensity.

(++) band corresponding to specific complex on the EMSA autoradiogram (See e.g., FIG. 2B, lane 5) easily discernible and of moderate intensity.

(+++) band corresponding to specific complex on the EMSA autoradiogram (See e.g., FIG. 2C, lane 6) easily discernible and of strong intensity.

This visual rating system is sufficient to analyze distinguishable differences and trends in the EMSA binding data as opposed to specific numerical values. If desired, the use of a phosphor imager or densitometer (commercially available from e.g., Bio-Rad Laboratories) could provide a means to assess the differences described here quantitatively. Specific visual ratings of binding affinities for the regulatory elements of oligonucleotide SEQ ID NOs 54–105 are shown in Tables 1–6 below (in the Tables, bold type face highlight the spacing nucleotides).

TABLE 1

Relative EMSA binding affinities for a series of regulatory elements in double stranded configurations (SEQ ID NOs. 54–65) having between 3–8 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 3 | TTCCGAA | – | – | – | – |
| 4 | TTCCCGAA | – | +++ | – | – |

TABLE 1-continued

Relative EMSA binding affinities for a series of regulatory elements in double stranded configurations (SEQ ID NOs. 54–65) having between 3–8 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 5 | TTCCCCGAA | + | – | +++ | ++ |
| 6 | TTCCCCCGAA | – | – | – | +++ |
| 7 | TTCCCCCCGAA | – | – | – | – |
| 8 | TTCCCCCCCGAA | – | – | – | – |

TABLE 2

Relative EMSA binding affinities for a series of regulatory elements in double stranded configurations (SEQ ID NOs. 66–75) having between 4–8 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCCGGAA | – | + | – | – |
| 5 | TTCCCGGAA | ++ | +++ | +++ | ++ |
| 6 | TTCCCCGGAA | – | – | – | +++ |
| 7 | TTCCCCCGGAA | – | – | – | – |
| 8 | TTCCCCCCGGAA | – | – | – | – |

TABLE 3

Relative EMSA binding affinities for a series of regulatory elements in double stranded configurations (SEQ ID NOs. 66–67 and 76–81) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCCGGAA | – | + | – | – |
| 5 | TTCCTGGAA | + | ++ | ++ | ++ |
| 6 | TTCCTTGGAA | – | – | – | +++ |
| 7 | TTCCTTTGGAA | – | – | – | – |

TABLE 4

Relative EMSA binding affinities for a series of regulatory elements in double stranded configurations (SEQ ID NOs. 82–89) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCCAGAA | – | + | – | – |
| 5 | TTCCCAGAA | + | ++ | +++ | ++ |
| 6 | TTCCCCAGAA | – | – | – | +++ |
| 7 | TTCCCCCAGAA | – | – | – | – |

TABLE 5

Relative EMSA binding affinities for a series of regulatory elements in double stranded configurations (SEQ ID NOs. 90–97) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCTTGAA | – | – | – | – |
| 5 | TTCTTTGAA | – | – | + | + |
| 6 | TTCTTTTGAA | – | – | – | + |
| 7 | TTCTTTTTGAA | – | – | – | – |

TABLE 6

Relative EMSA binding affinities for a series of regulatory elements of double stranded configurations (SEQ ID NOs. 98–105) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCTAGAA | – | – | – | – |
| 5 | TTCTCAGAA | – | – | ++ | ++ |
| 6 | TTCTCCAGAA | – | – | – | ++ |
| 7 | TTCTCCCAGAA | – | – | – | – |

In evaluating the data in Tables 1–6, one should be aware that IL-6 induces three specific DNA-binding complexes in HepG2 cells. P. Lamb et al., 83 *Blood* 2063 (1994). Accordingly, for the columns marked "IL-6," the complex being rated is the slowest-migrating IL-6-induced complex in the EMSA, i.e., the STAT3 homodimer (Z. Zhong et al., 264 *Science* 95), and thus is not reflective of complexes that contain STAT1μ, which is rated for the IFNγ complex. Further, when interpreting the results contained in Tables 1–6, the data should be analyzed for trends as opposed to specific numerical values. This is due to the inherent lack of fine sensitivity in the EMSA assay. This variability arises, at least in part, from differences in the quality of the nuclear extracts used, cell line differences, and variability in the protein concentration determinations.

The binding data summarized in Tables 1–6 show that DNA regulatory element sequences comprising different nucleotide spacing between the palindromic element (TT-space-AA) have surprisingly different affinities for the activated transcriptional regulatory proteins activated by IFNγ, IL-6, GM-CSF and IL-4 treatment of responsive host cells. Specifically, the four base pair spacing shows remarkable selectivity in its binding to the activated transcriptional regulatory protein complex induced by IL-6, i.e., STAT3. Further, this will hold true for other signaling molecules that activate STAT3, such as Oncostatin M, LIF, EGF, PDGF, G-CSF, IL-10, IL-11 and CNTF. The five base pair spacing shows little selectivity between the activated transcriptional regulatory protein complexes, but is noteworthy due to its affinity in most cases for all of the cytokine-induced complexes tested. The six base pair spacing again shows remarkable selectivity, but, in this case, in its binding to the activated transcriptional regulatory protein complex(es) induced by IL-4 (i.e. STAT5 and/or STAT6). The binding data further show that the exact identity of the spacing nucleotides also has some influence on binding affinity, i.e. spacing nucleotides rich in thymines and deoxyadenosines (SEQ ID NOs. 90–105) disfavor STAT1 and STAT3 binding (Tables 4–6). Thus, the elements with a five base pair spacer rich in thymines and deoxyadenosines were selective for the STAT complexes activated by GM-CSF and IL-4 (i.e., STAT5 and/or STAT6) over those containing STAT1α or STAT3.

For those oligonucleotides that were tested, the spacing preference of the STAT complexes activated by IL-2 in CTLL-2 cells, Epo in TF-1 cells, and IL-3 in NFS-60 cells is the same as for the complexes activated by GM-CSF in U937 cells. This is in accord with the fact that IL-2, GM-CSF, Epo and IL-3 all are reported to activate the same STAT protein, STAT5. The spacing preference for the STAT complexes activated by IL-13 in ME-180 cells was the same as for the STAT complexes activated by IL-4 in U-937 and ME-180 cells, and is due to the likelihood that IL-4 and IL-13 both activate the same STAT protein, STAT6.

In NFS-60 cells, G-CSF activated two STAT complexes that were distinguishable by their differing mobilities in an EMSA. The slower-migrating complex comigrated with the STAT3 homodimer stimulated by IL-6 and was shown to contain STAT3 by antibody supershift experiments using a specific STAT3 antiserum. The faster-migrating complex contained an unidentified STAT complex that migrated like the STAT complexes activated by IL-3 and GM-CSF. In binding experiments, for the oligonucleotide series that were tested, the G-CSF-activated STAT3-like complex had spacing preferences indistinguishable from the STAT3 homodimer induced by IL-6. Similarly, the G-CSF-activated STAT complex that comigrated with the GM-CSF- and IL-3-activated STAT complexes had the same corresponding spacing preferences.

Data are not shown in Tables 1–6 for the regulatory elements SEQ ID NOs. 106, 108 and 110. SEQ ID NO. 106 is a regulatory element that has a five base pair spacing and will bind to the STAT complexes activated by IFNγ(+++), IL-6(+++), GM-CSF(+++) and IL-4(+++). SEQ ID NO. 108 is a regulatory element that has a five base pair spacing and will bind to the STAT complexes activated by IFNγ(+++), IL-6(+), GM-CSF(+++) and IL-4(++). SEQ ID NO. 110 is a regulatory element that has a six base pair spacing and selectively bound to the STAT complex activated by IL-4(+++), but not to STAT complexes activated by IFNγ, IL-6 or GM-CSF. Thus, when tested for in vitro binding, SEQ ID NOs. 106, 108 and 110 also fit the spacing patterns described above.

A specific example of this nucleotide spacing effect can be seen with respect to the EMSA autoradiograms of FIGS. 2A–2D. In panel 2A, a radiolabeled, double-stranded oligonucleotide probe (corresponding to a four base pair spacer) made by annealing olignucleotides of SEQ ID NOs. 66 and 67 was used. Lanes marked 'UN' represent experiments using extracts from untreated cells. Other lanes are marked according to the inducing cytokine. Activated complexes can be identified by their absence in untreated extracts and their presence in extracts treated by cytokine. The only activated transcriptional regulatory protein complex that binds to this four-spacer probe can be seen in lane 3 (identified on FIG. 2A as the STAT3 homodimer), and corresponding to the IL-6-induced extract.

In panel 2B, a radiolabeled, double-stranded oligonucleotide probe (corresponding to a five base pair spacer) made by annealing olignucleotides of SEQ ID NOs 76 and 77 was used. Lanes marked 'UN' represent experiments using extracts from untreated cells. Other lanes are marked according to the inducing cytokine. This panel shows that IFNγ, IL-6, GM-CSF and IL-4 all activate transcriptional regulatory protein complexes that are bound by this probe. These activated complexes can be seen in lanes 2, 3, 5 and 6 and are the various complexes are identified on FIG. 2B.

In panel 2C, a radiolabeled, double-stranded oligonucleotide probe (corresponding to a six base pair spacer) made by annealing olignucleotides of SEQ ID NOs 78 and 79 was used. Lanes marked 'UN' represent experiments using extracts from untreated cells. Other lanes are marked according to the inducing cytokine. The only activated transcriptional regulatory protein complex that binds to this six-spacer probe can be seen in lane 6 (identified FIG. 2C), the IL-4-induced extract.

In panel 2D, a radiolabeled, double-stranded oligonucleotide probe (corresponding to a seven base pair spacer) made by annealing olignucleotides of SEQ ID NOs 80 and 81 was used. Lanes marked 'UN' represent experiments using extracts from untreated cells. Other lanes are marked according to the inducing cytokine. Only complexes that bind constituitively (marked on FIG. 2D) can be detected using this seven-spacer probe; no cytokine-activated transcriptional regulatory protein complexes are apparent.

Transient transfection assays

Figure 1B:
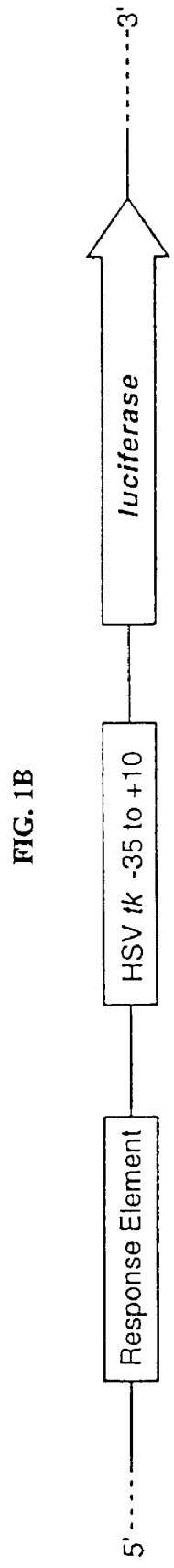

The reporter plasmids SEQID56x4TK-LUC, SEQID68x4TK-LUC, SEQID106x4TK-LUC, SEQID70x4TK-LUC, SEQID108x6TK-LUC, and SEQID110x4TK-LUC contain four copies (or six copies for SEQID 108x6TK-LUC) of oligonucleotide sequences with the indicated SEQ ID NOs linked to the promoter of the Herpes Simplex virus thymidine kinase gene at position −35 with respect to the cap site. See FIG. 1. The reference reporter, TK-LUC (P. Lamb et al., 8 Blood 2063 (1994)), the disclosure of which is herein incorporated by reference, is the parent vector that contains no regulatory element. These chimeric promoters drive the expression of the structural gene for firefly luciferase.

HepG2 and ME-180 cells were transfected with the reporter plasmids of above by calcium phosphate coprecipitation. Cells were seeded at 1–4×10$^5$/ml the day before transfection. Cells were exposed to a calcium phosphate precipitate containing the above reporter plasmids (10–20 μg/ml) and the β-galactosidase-expressing plasmid pCH110 (5 μg/ml, commercially available from Pharmacia Biotech, Piscataway, N.J.) for 6 h (HepG2) or 12 h (ME-180). The medium was then changed and the cells allowed to recover for 16–18 h. Recombinant cytokines were then added prediluted in growth medium and the cells harvested after 5 h (HepG2) or 6 h (ME-180). Cells were lysed and luciferase and p-galactosidase activities determined using standard techniques. See, e.g. J. R. De Wet et al., 7 Mol. Cell. Biol. 725 (1987) and Sambrook et al., Molecular Cloning: A Laboratory Manual 2nd ed., Cold Spring Harbor Laboratory Press, Cold Spring Harbor, N.Y. (1989), the disclosure of which is herein incorporated by reference. For each sample the normalized response was determined by dividing light units obtained from the luciferase assay with the β-galactosidase activity in the same lysate as determined using a chromogenic substrate. The results of these transfections are shown below in Tables 7–8. Numbers given are the mean fold inductions ('fold induction' is defined as the normalized response in a cytokine-treated sample divided by the normalized response in an untreated sample).

TF-1 cells were transfected with the reporter plasmids of above by the DEAE-dextran method as described by J. Suzow and A. D. Friedman, 13 Mol. Cell. Biol., 2141 (1993), the disclosure of which is herein incorporated by reference, with the following modifications: test reporter constructs were added to a concentration of 3 μg/mL during the transfection, pMSVCAT vector was not added to the transfection mixtures, the growth medium used was as described above for TF-1 cells, and cytokine inductions were carried out for 4–5 h. Cells were lysed and luciferase activity determined using standard techniques. Transfections were performed in a batch, and identical numbers of transfected cells were then separately induced with cytokine for the 4–5 h induction period. Numbers given are the mean fold inductions ('fold induction' for TF-1 transfections is defined as the luciferase response in a cytokine-treated sample divided by the luciferase response in an untreated sample). The results of these transfections are shown in Table 9.

NFS-60 cells were transfected with the reporter plasmids described above by the DEAE-dextran method as described in the preceding paragraph with the following modifications: test reporter constructs were added to a concentration of 6 μg/mL during the transfection, and cytokine inductions were carried out for 2.5 h. The results of these transfections are shown in Table 10.

TABLE 7

Transcriptional Induction in HepG2 Cells of Reporter Constructs Incorporating Multiple Copies of STAT-Selective Regulatory Elements. The values given are mean fold inductions in response to the indicated cytokine. The value in the parentheses is the number of experiments included to calculate the mean.

| Reporter | Core Element | IFNγ | IL-6 | Oncostatin M |
|---|---|---|---|---|
| TK-LUC | none | 1.0 (3) | 1.8 (3) | 2.9 (3) |
| SEQID56x4TK-LUC | TTCCCGAA | 0.8 (3) | 9.7 (3) | 20 (3) |
| SEQID68x2TK-LUC | TTCCCGGAA | 34 (3) | 19 (3) | 30 (3) |
| SEQID106x4TK-LUC | TTCCCCGAA | 60 (3) | 43 (3) | 90 (3) |
| SEQID70x4TK-LUC | TTCCCCGGAA | 0.8 (3) | 0.9 (3) | 1.0 (3) |
| SEQID110x4TK-LUC | TTCCCAAGAA | 0.9 (3) | 1.8 (3) | 3.2 (3) |

TABLE 8

Transcriptional Induction in ME-180 Cells of Reporter Constructs Incorporating Multiple Copies of STAT-Selective Regulatory Elements. The values given are mean fold inductions in response to the indicated cytokine. The value in the parentheses is the number of experiments included to calculate the mean.

| Reporter | Core Element | IFNγ | IL-6 | Oncostatin M | IL-4 |
|---|---|---|---|---|---|
| TK-LUC | none | 1.0 (3) | 1.2 (3) | 1.3 (3) | 0.9 (3) |
| SEQID-56x4TK-LUC | TTCCCGAA | 1.2 (3) | 2.4 (3) | 4.3 (3) | 1.4 (3) |
| SEQID-68x2TK-LUC | TTCCCGGAA | 3.7 (3) | 3.0 (3) | 5.1 (3) | 1.2 (3) |
| SEQID-106x4TK-LUC | TTCCCCGAA | 5.5 (3) | 4.5 (3) | 11 (3) | 1.0 (3) |
| SEQID-70x4TK-LUC | TTCCCCGGAA | 1.1 (3) | 1.3 (3) | 1.4 (3) | 1.2 (3) |
| SEQID-110x4TK-LUC | TTCCCAAGAA | 1.0 (3) | 1.4 (3) | 1.2 (3) | 8.1 (3) |

TABLE 10

Transcriptional Induction in NFS-60 Cells of Reporter Constructs Incorporating Multiple Copies of STAT-Selective Regulatory Elements. The values given are mean fold inductions in response to the indicated cytokine. The value in the parentheses is the number of experiments included to calculate the mean.

| Reporter | Core Element | G-CSF | IL-3 | IL-6 |
|---|---|---|---|---|
| SEQID56x4TK-LUC | TTCCCGAA | 13.8 (2) | 1.0 (2) | 4.1 (2) |
| SEQID68x2TK-LUC | TTCCCGGAA | 23.8 (2) | 3.5 (2) | 4.8 (2) |
| SEQID106x4TK-LUC | TTCCCCGAA | 23.6 (2) | 6.1 (2) | 6.9 (2) |
| SEQID110x4TK-LUC | TTCCCAAGAA | 1.0 (1) | 1.0 (1) | n.d. | n.d. = not determined

One of the regulatory elements that was incorporated into the TK-LUC reporter construct used to generate the data in Tables 7–10 (SEQID 106) was taken from the promoter of the human IRF-1 gene, a gene reported to be regulated by IFNγ, and, in light of the teaching of the present invention, can be seen as a natural counterpart to the five base pair synthetic spacing elements in Tables 1–6. One of the regulatory elements that was incorporated into the TK-LUC reporter construct used to generate the data in Tables 7–9 (SEQID 108) was taken from the promoter of the human FcεRIIb gene, and, in light of the teaching of the present invention, can be seen as a natural counterpart to the five base pair synthetic spacing elements in Tables 1–6. One of the regulatory elements that was incorporated into the TK-LUC reporter construct used to generate the data in Tables 7–10 (SEQID 110) was taken from the promoter of the human Cε gene, a gene reported to be regulated by IL-4, and, in light of the teaching of the present invention, can be seen as a natural counterpart to the six base pair synthetic spacing elements in Tables 1–6.

Table 7 shows that the binding data for the IFNγ- and IL-6-activated transcriptional regulatory protein complexes shown in Tables 1–6 correlate with selective activation of transcription. Thus, a four nucleotide spacing regulatory element not only selectively binds the IL-6-induced activated transcriptional regulatory protein complex but, when placed in a functional promoter upstream of a reporter gene, selectively activates the reporter gene transcription. Oncostatin M also activates STAT3 and thus also stimulates transcription from the palindromic element with a spacing of four (SEQ ID NO. 56), as will other signaling molecules that activate STAT3. The five nucleotide spacing elements (SEQ ID NOs. 68 and 106) bind both the IFNγ,- and IL-6-induced transcriptional regulatory protein complexes and, correspondingly, also confer responsiveness to IFNγ, IL-6

TABLE 9

Transcriptional Induction in TF-1 Cells of Reporter Constructs Incorporating Multiple Copies of STAT-Selective Regulatory Elements. The values given are mean fold inductions in response to the indicated cytokine. The value in the parentheses is the number of experiments included to calculate the mean.

| Reporter | Core Element | IL-4 | IL-6 | GM-CSF | Epo | IL-3 |
|---|---|---|---|---|---|---|
| TK-LUC | none | 0.7 (2) | 1.2 (2) | 0.8 (2) | 0.8 (2) | 0.7 (2) |
| SEQID56x4TK-LUC | TTCCCGAA | 0.7 (1) | 5.5 (2) | 1.2 (2) | 0.6 (2) | n.d. |
| SEQID68x4TK-LUC | TTCCCGGAA | n.d. | 19 (1) | 3.4 (2) | 1.8 (2) | 2.8 (2) |
| SEQID106x4TK-LUC | TTCCCCGAA | 1.4 (2) | 43 (3) | 9.6 (4) | 3.1 (4) | 6.8 (3) |
| SEQID108x6TK-LUC | TTCTAAGAA | n.d. | 3.1 (1) | 7.6 (2) | 3.5 (2) | 7.3 (2) |
| SEQID110x4TK-LUC | TTCCCAAGAA | 3.3 (3) | 1.3 (1) | 1.3 (2) | 0.8 (2) | 1.3 (2) | n.d. = not determined and Oncostatin M when placed in the requisite reporter construct. The six nucleotide spacing elements (SEQ ID NOs. 70 and 110) bind the IFNγ- and IL-6-induced activated transcriptional regulatory protein complexes weakly, and, correspondingly do not confer responsiveness in the context of a reporter construct to IFNγ, and confers much lower responsiveness in the context of a reporter construct to IL-6 and Oncostatin M. Thus, the binding selectivity of the palindromic elements correlates directly with the transcriptional activation potential of the regulatory elements of the present invention.

The transfection results for the reporter constructs in ME-180 cells are shown in Table 8. The element with a four base pair spacing (SEQ ID NO. 56) again selectively mediated transcriptional induction by IL-6 and OSM, activators of STAT3. The reporters containing the five base pair spacing elements (SEQ ID NOs. 68, 106 and 108) again responded to IFNγ, IL-6, and OSM; however, they did not respond to IL-4 though they bound to the IL-4-activated STAT complex. The reporter containing the six base pair synthetic spacing element (SEQ ID NO. 70) did not respond to any of the cytokines tested (though it bound specifically to the IL-4-activated STATs), but the natural Cε element with a six base pair spacing (SEQ ID NO. 110) mediated strong and extremely selective transcriptional induction by IL-4, and is therefore a functional activation site in accord with the in vitro binding data.

The transfection results for reporter constructs in TF-1 cells are shown in Table 9. The results are substantially consistent with the in vitro binding data described above. Thus, the element with a four base pair spacing (SEQ ID NO. 56) was unresponsive to IL-4, Epo, IL-3 and GM-CSF but did respond to IL-6, while the reporters containing the five base pair spacing elements (SEQ ID NOs. 68, 106 and 108) responded to IL-6, Epo, IL-3 and GM-CSF but not to IL-4. Accordingly, the reporter containing the natural six base pair spacing element (SEQ ID NO. 110) responded to IL-4 but not to IL-6, Epo, IL-3 or GM-CSF.

The transfection results for the reporter constructs tested in NFS-60 cells are shown in Table 10. The results are substantially consistent with the in vitro binding data described above. Thus, the element with a four base pair spacing (SEQ ID NO. 56) mediated a response to both IL-6 and G-CSF (both of which activate STAT3), while the elements with a five base pair spacing (SEQ ID NOs. 68 and 108), both of which bind to both STAT complexes activated by G-CSF, mediated a response to IL-3, IL-6 and G-CSF (in accord with the in vitro binding data). Accordingly, the reporter containing the natural six base pair spacing element (SEQ ID 110) did not respond to IL-3 or G-CSF.

EXAMPLE 2

Preparation of the reagents, cells, cell culture, nuclear extracts and Electrophoretic Mobility Shift Assays were performed as described in Example 1, with the exception that the double-stranded probe oligonucleotides used in the Electrophoretic Mobility Shift Assays (EMSAs) were formed by annealing oligonucleotides with the sequences:

| | | |
|---|---|---|
| 5'-GATCTGCTTACGTAACGT | -3' | (SEQ ID NO. 112) |
| 3'-     ACGAATGCATTGCACTAG | -5' | (SEQ ID NO. 113) |
| 5'-GATCTGCTTACCGTAACGT | -3' | (SEQ ID NO. 114) |
| 3'-     ACGAATGGCATTGCACTAG | -5' | (SEQ ID NO. 115) |
| 5'-GATCTGCTTACCCGTAACGT | -3' | (SEQ ID NO. 116) |
| 3'-     ACGAATGGGCATTGCACTAG | -5' | (SEQ ID NO. 117) |
| 5'-GATCTGCTTACCCCGTAACGT | -3' | (SEQ ID NO. 118) |
| 3'-     ACGAATGGGGCATTGCACTAG | -5' | (SEQ ID NO. 119) |
| 5'-GATCTGCTTCCGTAACGT | -3' | (SEQ ID NO. 120) |
| 3'-     ACGAAGGCATTGCACTAG | -5' | (SEQ ID NO. 121) |
| 5'-GATCTGCTTCCCGTAACGT | -3' | (SEQ ID NO. 122) |
| 3'-     ACGAAGGGCATTGCACTAG | -5' | (SEQ ID NO. 123) |
| 5'-GATCTGCTTCCCCGTAACGT | -3' | (SEQ ID NO. 124) |
| 3'-     ACGAAGGGGCATTGCACTAG | -5' | (SEQ ID NO. 125) |
| 5'-GATCTGCTTCCCCCGTAACGT | -3' | (SEQ ID NO. 126) |
| 3'-     ACGAAGGGGGCATTGCACTAG | -5' | (SEQ ID NO. 127) |
| 5'-GATCTGCTTCTGTAACGT | -3' | (SEQ ID NO. 128) |
| 3'-     ACGAAGACATTGCACTAG | -5' | (SEQ ID NO. 129) |
| 5'-GATCTGCTTCTCGTAACGT | -3' | (SEQ ID NO. 130) |
| 3'-     ACGAAGAGCATTGCACTAG | -5' | (SEQ ID NO. 131) |
| 5'-GATCTGCTTCTCCGTAACGT | -3' | (SEQ ID NO. 132) |
| 3'-     ACGAAGAGGCATTGCACTAG | -5' | (SEQ ID NO. 133) |
| 5'-GATCTGCTTCTCCCGTAACGT | -3' | (SEQ ID NO. 134) |
| 3'-     ACGAAGAGGGCATTGCACTAG | -5' | (SEQ ID NO. 135) | where the nucleotide sequences shown in bold type face correspond to nucleotide sequences, including their double-stranded complement, tested for activity as regulatory elements according to the present invention.

Relative binding affinities, as determined from the EMSA results for oligonucleotide SEQ ID NOs 112–135, were visually rated and assigned according to the same visual rating scale as described in Example 1.

This visual rating system is sufficient to analyze distinguishable differences and trends in the EMSA binding data as opposed to specific numerical values. If desired, the use of a phosphor imager or densitometer (commercially available from e.g., Bio-Rad Laboratories) could provide a means to assess the differences described here quantitatively. Specific visual ratings of binding affinities for the regulatory elements of oligonucleotide SEQ ID NOs 1 12–135 are shown in Tables 11–13 below (in the Tables, bold type face highlight the spacing nucleotides).

TABLE 11

Relative EMSA binding affinities for a series of regulatory elements of double stranded configurations (SEQ ID NOs. 114–121) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTACGTAA | − | − | − | − |
| 5 | TTACCGTAA | + | ++ | − | − |
| 6 | TTACCCGTAA | − | − | + | + |
| 7 | TTACCCCGTAA | − | − | − | ++ |

TABLE 12

Relative EMSA binding affinities for a series of regulatory elements of double stranded configurations (SEQ ID NOs. 122–129) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCCGTAA | − | − | − | − |
| 5 | TTCCCGTAA | + | ++ | − | − |

TABLE 12-continued

| 6 | TTCCCCGTAA  | – | – | + | + |
| 7 | TTCCCCCGTAA | – | – | – | + |

TABLE 13

Relative EMSA binding affinities for a series of regulatory elements of double stranded configurations (SEQ ID NOs. 130–137) having between 4–7 spacing deoxynucleotides in response to the cytokines IFNγ, IL-6, GM-CSF (GM = GM-CSF) and IL-4.

| Spacing (x) | Core Regulatory Element Series TTN$_x$AA | IFNγ | IL-6 | GM | IL-4 |
|---|---|---|---|---|---|
| 4 | TTCTGTAA     | –  | +   | –  | –  |
| 5 | TTCTCGTAA    | +  | ++  | –  | –  |
| 6 | TTCTCCGTAA   | –  | –   | ++ | +  |
| 7 | TTCTCCCGTAA  | –  | –   | –  | ++ |

In evaluating the data in Tables 11–13, one should be aware of the that IL-6 induces three specific DNA-binding complexes in HepG2 cells. P. Lamb et al., 8 *Blood* 2063 (1994). Accordingly, for the columns marked "IL-6," the complex being rated is the slowest-migrating IL-6-induced complex in the EMSA, i.e., the STAT3 homodimer (Z. Zhong et al., 264 *Science* 95), and thus is not reflective of complexes that contain STAT1, which is rated for the IFNγ complex. Further, when interpreting the results contained in Tables 11–13, the data should be analyzed for trends as opposed to specific numerical values. This is due to the inherent lack of fine sensitivity in the EMSA assay. This variability arises, at least in part, from differences in the quality of the nuclear extracts used, cell line differences, and variability in the protein concentration determinations. The binding affinities of STAT complexes for the oligonucleotides in Tables 11–13 were generally lower (by roughly 10-fold or more) than for the series described in Example 1.

The binding data summarized in Tables 11–13 show that DNA regulatory element sequences comprising different nucleotide spacings between the palindromic (TT-space-AA) element have surprisingly different affinities for the activated transcriptional regulatory proteins activated by IFNγ, IL-6, GM-CSF and IL-4 treatment of responsive cells. For the spacing elements where one or both core half sites is 'TTA', the spacing preferences of some STAT complexes are subtly different from those described in Example 1. In general, the four base pair spacing did not bind any complexes except in one instance (Table 13) in which the STAT3-containing complex (IL-6-activated) was selectively bound, consistent with the data shown in Example 1. STAT1- and STAT3-containing complexes (activated by IFNγ or IL-6) bound to the five base pair spacing in each series. For these series of 'TTA' core half site-containing elements, the binding preference for the STAT complexes activated by GM-CSF is a six base pair spacing (instead of five base pair spacing as shown in Example 1). The IL-4-activated STAT complexes also can bind to these six base pair spacing elements, but now the seven base pair spacing selectively binds the IL-4-activated STAT complexes. Therefore, unlike for STAT1- and STAT3-containing complexes, the spacing preference for the GM-CSF- and IL-4-activated STAT complexes has been expanded by one nucleotide when one or both of the core half sites is 5'-TTA-3'. This shift in spacing preference rendered the regulatory elements in this Example 2 with a spacing of five base pair selective for STAT1 and/or STAT3 over the STAT complexes activated by GM-CSF or IL-4. Thus, the nature of the internal nucleotides can affect not only the absolute binding affinity of a given STAT complex (c.f. Tables 4–6 and 11–13) but also can affect the spacing preference of the various STAT complexes (Tables 11–13).

For those oligonucleotides that were tested, the spacing preference of the STAT complexes activated by IL-2 in CTLL-2 cells is the same as for the complexes activated by GM-CSF in U937 cells. This is in accord with the fact that IL-2 and GM-CSF activate the same STAT protein, STAT5. The spacing preference for the STAT complexes activated by IL-13 in ME-180 cells was the same as for the STAT complexes activated by IL-4 in U-937 and ME-180 cells and is due to the likelihood that IL-4 and IL-13 both activate the same STAT protein, STAT6.

In NFS-60 cells, G-CSF activated two STAT complexes that were distinguishable by their differing mobilities in an EMSA. The slower-migrating complex comigrated with the STAT3 homodimer stimulated by IL-6 and was shown to contain STAT3 by antibody supershift experiments using a specific STAT3 antiserum. The faster-migrating complex contained an unidentified STAT complex that migrated like the STAT complexes activated by GM-CSF. In binding experiments, for the oligonucleotide series that were tested, the G-CSF-activated STAT3-like complex had spacing preferences indistinguishable from the STAT3 homodimer induced by IL-6. Similarly, the G-CSF-activated STAT complex that comigrated with the GM-CSF-activated STAT complexes had the same corresponding spacing preferences.

EXAMPLE 3

Preparation of the reagents, cells, cell culture, nuclear extracts and Electrophoretic Mobility Shift Assays were performed as described in Example 1, with the exception that, in addition to some mentioned already in Example 1, the double-stranded probe oligonucleotides used in the Electrophoretic Mobility Shift Assays (EMSAs) were formed by annealing oligonucleotides with the sequences:

| | |
|---|---|
| 5'-GATCTGCTTCCCAAGAACGT | -3' (SEQ ID NO. 136) |
| 3'-          ACGAAGGGTTCTTGCACTAG | -5' (SEQ ID NO. 137) |
| 5'-GATCCACTTCCCCGGAACAGA | -3' (SEQ ID NO. 138) |
| 3'-         GTGAAGGGGCCTTGTCTCTAG | -5' (SEQ ID NO. 139) |
| 5'-GATCCACTTCCCCAGAACAGA | -3' (SEQ ID NO. 140) |
| 3'-         GTGAAGGGGTCTTGTCTCTAG | -5' (SEQ ID NO. 141) |
| 5'-GATCCACTTCCCAGGAACAGA | -3' (SEQ ID NO. 142) |
| 3'-         GTGAAGGGTCCTTGTCTCTAG | -5' (SEQ ID NO. 143) |
| 5'-GATCTACTTCCCAAGAACAGA | -3' (SEQ ID NO. 144) |
| 3'-         ATGAAGGGTTCTTGTATCTAG | -5' (SEQ ID NO. 145) |
| 5'-GATCCGCTTCCCAAGAACGGA | -3' (SEQ ID NO. 146) |
| 3'-         GCGAAGGGTTCTTGCCTCTAG | -5' (SEQ ID NO. 147) |
| 5'-GATCCACTTCTTAAGAACAGA | -3' (SEQ ID NO. 148) |
| 3'-         GTGAAGAATTCTTGTCTCTAG | -5' (SEQ ID NO. 149) |
| 5'-GATCCACTTTCCAAGAACAGA | -3' (SEQ ID NO. 150) |
| 3'-         GTGAAAGGTTCTTGTCTCTAG | -5' (SEQ ID NO. 151) | the nucleotide sequences shown in bold type face correspond to nucleotide sequences, including their double-stranded complement, tested for activity as regulatory elements according to the present invention.

Relative binding affinities, as determined from the EMSA results for oligonucleotides listed below, were visually rated and assigned according to the same visual rating scale as described in Example 1.

This visual rating system is sufficient to analyze distinguishable differences and trends in the EMSA binding data as opposed to specific numerical values. If desired, the use of a phosphor imager or densitometer (commercially available from e.g., Bio-Rad Laboratories) could provide a means to assess the differences described here quantitatively. Specific visual ratings of binding affinities for the regulatory elements of oligonucleotide SEQ ID NOs 58–59, 68–69, 70–71, 86–87, 100–101, 106–107, 108–109, 110–111, and 136–150 are shown in Table 14 below (in Table 14, type face highlight the core sequences).

TABLE 14

Relative EMSA binding affinities for a series of regulatory elements (core plus some flanking sequences) differing in flanking and spacing sequences to transcriptional regulatory proteins activated in response to the cytokines IL-4 and IL-13.

| SEQ ID | Regulatory Element | IL-4 | IL-13 |
|---|---|---|---|
| 110 | CACTTCCCAAGAACAGA | +++ | +++ |
| 70 | TGCTTCCCCGGAACGT | ++ | ++ |
| 86 | TGCTTCCCCAGAACGT | + | + |
| 136 | TGCTTCCCAAGAACGT | ++ | ++ |
| 138 | CACTTCCCCGGAACAGA | ++ | ++ |
| 140 | CACTTCCCCAGAACAGA | ++ | ++ |
| 142 | CACTTCCCAGGAACAGA | ++ | ++ |
| 144 | TACTTCCCAAGAACATA | ++ | ++ |
| 146 | CGCTTCCCAAGAACGGA | ++ | ++ |
| 148 | CACTTCTTAAGAACAGA | ++ | ++ |
| 150 | CACTTTCCAAGAACAGA | ++ | ++ |
| 58 | TGCTTCCCCGAACGT | ++ | n.d. |
| 68 | TGCTTCCCGGAACGT | ++ | ++ |
| 100 | TGCTTCTCAGAACGT | ++ | ++ |
| 106 | GATTTCCCCGAAATG | ++ | ++ |
| 108 | CAATTTCTAAGAAAGGA | ++ | n.d. | n.d. = not determined

The data in Table 13 show that the IL-4 and IL-13-activated STAT complexes can bind to all of the listed sequences with similar affinity (with the exception of SEQ ID NO. 86, which was slightly lower in affinity). These data are fully consistent with the binding data described in Example 1 herein.

Transient transfection assays

The reporter plasmids SEQID58x4-TK-LUC, SEQID68x4-TK-LUC, SEQID70x4-TK-LUC, SEQ D100x4-TK-LUC, SEQID106x4-TK-LUC, SEQID108x4-TK-LUC, SEQID110x4-TK-LUC, SEQID86x4-TK-LUC, SEQID136x4-TK-LUC, SEQID138x4-TK-LUC, SEQID140x4-TK-LUC, SEQID 142x4-TK-LUC, SEQID144x4-TK-LUC, SEQID146x4-TK-LUC, SEQID148x4-TK-LUC, and SEQID150x4-TK-LUC contain four copies of oligonucleotide sequences with the indicated SEQ ID NOs linked to the promoter of the Herpes Simplex virus thymidine one at position −35 with respect to the cap site. See FIG. 1. The reference TK-LUC (P. Lamb et al., 83 *Blood* 2063 (1994)), the disclosure of which is herein incorporated by reference, contains the simple Herpes Simplex virus thymidine kinase promoter with no regulatory element. These chimeric promoters drive the expression of the structural gene for firefly luciferase.

ME-180 cells were transfected with the reporter plasmids of above by calcium phosphate coprecipitation as described in Example 1. The results of these transfections are shown below in Tables 15 and 16. Numbers given are the mean fold inductions ('fold induction' is defined as the normalized response in a cytokine-treated sample divided by the normalized response in an untreated sample).

TABLE 15

Transcriptional induction in ME-180 cells of reporter constructs incorporating IL-4/IL-13-selective regulatory elements showing effect of flanking and spacing sequence (core sequence highlighted). The values given are mean fold inductions in response to the indicated cytokine. The value in the parentheses is the number of experiments included to calculate the mean.

| Reporter | Core Element | IL-4 | IL-13 |
|---|---|---|---|
| TK-LUC | none | 0.9 (3) | 1.0 (3) |
| SEQID110x4TK-LUC | CACTTCCCAAGAACAGA | 22 (3) | 9.7 (3) |
| SEQID70x4TK-LUC | TGCTTCCCCGGAACGT | 1.3 (3) | 1.0 (3) |
| SEQID86x4TK-LUC | TGCTTCCCCAGAACGT | 1.2 (3) | 1.1 (3) |
| SEQID136x4TK-LUC | TGCTTCCCAAGAACGT | 1.5 (3) | 1.2 (3) |
| SEQID138x4TK-LUC | CACTTCCCCGGAACAGA | 2.7 (3) | 1.6 (3) |
| SEQID140x4TK-LUC | CACTTCCCCAGAACAGA | 8.0 (3) | 3.0 (3) |
| SEQID142x4TK-LUC | CACTTCCCAGGAACAGA | 10 (3) | 6.4 (3) |
| SEQID144x4TK-LUC | TACTTCCCAAGAACATA | 3.0 (3) | 1.5 (3) |
| SEQID146x4TK-LUC | CGCTTCCCAAGAACGGA | 1.5 (3) | 1.3 (3) |
| SEQID148x4TK-LUC | CACTTCTTAAGAACAGA | 7.3 (3) | 3.3 (3) |
| SEQID150x4TK-LUC | CACTTTCCAAGAACAGA | 1.2 (3) | 1.1 (3) |

TABLE 16

Regulatory elements with a five base pair spacing that bind to the IL-4-Activated STAT complexes do not mediate transcriptional induction in ME-180 cells treated with IL-4 (spacing nucleotides highlighted). The values given are mean fold inductions in response to the indicated cytokine. The value in the parentheses is the number of experiments included to calculate the mean.

| Reporter | Core Element | IL-4 |
|---|---|---|
| SEQID58x4TK-LUC | TGCTTCCCCGAACGT | 1.2 (3) |
| SEQID68x4TK-LUC | TGCTTCCCGGAACGT | 1.1 (3) |
| SEQID100x4TK-LUC | TGCTTCTCAGAACGT | 1.2 (3) |
| SEQID106x4TK-LUC | GATTTCCCCGAAATG | 0.8 (3) |
| SEQID108x4TK-LUC | CAATTTCTAAGAAAGGA | 0.8 (3) |
| SEQID150x4TK-LUC | CACTTTCCAAGAACAGA | 1.2 (3) |

The data summarized in Table 15 demonstrate that the identity of the spacing nucleotides and flanking nucleotides influence whether or not a given regulatory sequence will be transcriptionally active (defined herein as greater than a two fold induction). In general, the responses in ME-180 cells to IL-13 were lower than to IL-4, probably reflecting a lower number of IL-13 receptors on ME-180 cells (this correlates with less STAT complex being activated by IL-13 as compared to IL-4). The effect of the flanking nucleotides is shown especially well by comparing the SEQ ID NO. 140x4TK-LUC entry with the SEQ ID NO. 70x4TK-LUC entry. SEQ ID NO. 140x4TK-LUC is activated by IL-4, while SEQ ID NO. 70x4TK-LUC is not, and the only difference between SEQ ID NO. 140 and SEQ ID NO. 70 are the two nucleotides on the 5' and 3' flanks of the core element. The data summarized in Table 16 demonstrate that for all of the tested response elements with a three base pair spacing, though they bind well to the IL-4-activated STAT complexes, they surprisingly do not mediate a transcriptional response in ME-180 cells in the context of the TK minimal promoter. This is true even if the flanking nucleotides are "optimal" (taken from SEQ ID NO. 110) as shown in Tables 15 and 16 for the entries for SEQ ID NO. 150x4TK-LUC. Thus, although all of the sequences shown in Tables 15 and 16 are capable of binding the STAT complexes activated by IL-4 and IL-13 (shown in Table 14), not all mediate a transcriptional induction in response to IL-4 or IL-13 (defined as greater than two fold induction). Nevertheless, because the ability of a regulatory element to bind to a given STAT complex is a prerequisite for that sequence to be transcriptionally active, the observed spacing preferences are thus an important determinant of selective transcriptional activation.

From the data in Table 15, it is possible to identify a general sequence that will not only bind the IL-4 and IL-13 activated STAT complexes selectively, but, importantly, will also mediate a transcriptional induction in response to IL-4 and IL-13. That general sequence is: 5'-ANTTCNNNNGAANA-3'(SEQ ID NO. 152)[and its double-stranded complement: 5-'-TNTTCNNNNGAANT-3' (SEQ ID NO. 153)], where N is a nucleotide independently selected from A, T, C or G. This sequence includes nucleotides outside of the core element that, from the data in Table 15, have been shown to influence transcriptional activation. Accordingly, preferred oligonucleotide sequences selective for IL-4 and IL-13 are selected from the group consisting of ACTTCCCAAGAACA (SEQ ID NO. 154), TGTTCTTGGGAAGT (SEQ ID NO. 155), ACTTCCCCGGAACA (SEQ ID NO. 156), TGTTCCGGGGAAGT (SEQ ID NO. 157), ACTTCCCCAGAACA (SEQ ID NO. 158), TGTTCTGGGGAAGT (SEQ ID NO. 159), ACTTCCCAGGAACA (SEQ ID NO. 160), TGTTCCTGGGAAGT (SEQ ID NO. 161), ACTTCCCAAGAACA (SEQ ID NO. 162), TGTTCTTGGGAAGT (SEQ ID NO. 163), ACTTCTTAAGAACA (SEQ ID NO. 164), and TGTTCTTAAGAAGT (SEQ ID NO. 165).

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A DNA construct comprising a cytokine-responsive regulatory element operably linked to a promoter, which promoter is operably linked to a heterologous coding sequence, wherein the coding sequence is under the transcriptional control of the regulatory element and the promoter, and further wherein the regulatory element has a nucleotide sequence selected from the group consisting of TTCNNGAA (SEQ ID NO. 5), TTAN$_y$TAA (SEQ ID NO. 13) and TTCN$_y$TAA (SEQ ID NO. 166), where N is independently selected from A,T,C or G and y is 3 or 4.

2. The DNA construct according to claim 1 wherein the regulatory element has the nucleotide sequence TTCNNGAA (SEQ ID NO. 5).

3. The DNA construct according to claim 1 wherein the regulatory element has the nucleotide sequence TTAN$_3$TAA.

4. The DNA construct according to claim 1 wherein the regulatory element has the nucleotide sequence TTAN$_4$TAA (SEQ ID NO. 13).

5. The DNA construct according to claim 1 wherein the regulatory element has the nucleotide sequence TTCN$_3$TAA.

6. The DNA construct according to claim 1 wherein the regulatory element has the nucleotide sequence TTCN$_4$TAA (SEQ ID NO. 166).

7. The DNA construct of claim 1 wherein the promoter is selected from the group consisting of a Herpes simplex virus thymidine kinase gene promoter, a adenovirus Elb gene promoter and a yeast alcohol dehydrogenase gene promoter.

8. The DNA construct of claim 1 wherein the heterologous coding sequence encodes a protein selected from the group consisting of luciferase, chloramphenicol acetyl transferase, β-galactosidase, secreted placental alkaline phosphatase, human growth hormone, t-PA, green flourescent protein and interferon.

9. The DNA construct of claim 1 wherein the promoter is a Herpes simplex virus thymidine kinase gene promoter and the heterologous coding sequence encodes luciferase.

10. A cultured or isolated host cell transfected with the DNA construct of claim 1.

11. A DNA construct comprising a cytokine-responsive regulatory element operably linked to a promoter, which promoter is operably linked to a heterologous coding sequence, wherein the gene is under the transcriptional control of the regulatory element and promoter, and further wherein the regulatory element has a nucleotide sequence selected from the group consisting of TTCCCGAA (SEQ ID NO. 22), TTCCCCCGAA (SEQ ID NO. 24), TTCCGGAA (SEQ ID NO. 25), TTCCCCGGAA (SEQ ID NO. 27), TTCCTTGGAA (SEQ ID NO. 29), TTCCAGAA (SEQ ID NO. 30), TTCCCCAGAA (SEQ ID NO. 32), TTCTTTGAA (SEQ ID NO. 33), TTCTTTTGAA (SEQ ID NO. 34), TTCTCCAGAA (SEQ ID NO. 36), TTACCGTAA (SEQ ID NO. 37), TTACCCGTAA (SEQ ID NO. 38), TTCCCGTAA (SEQ ID NO. 40), TTCCCCGTAA (SEQ ID NO. 41), TTCTGTAA (SEQ ID NO. 43), TTCTCGTAA (SEQ ID NO. 44), TTCTCCGTAA (SEQ ID NO. 45), TTTCCCG-TAA (SEQ ID NO. 48), TTCCCAGGAA (SEQ ID NO. 49), and TTCTTAAGAA (SEQ ID NO. 50).

12. The DNA construct of claim 11 comprising more than one copy of said regulatory element.

13. The DNA construct of claim 12 wherein each copy of said regulatory element has the same nucleotide sequence.

14. The DNA construct of claim 11 wherein the promoter is selected from the group consisting of a Herpes simplex virus thymidine kinase gene promoter, a adenovirus E1b gene promoter and a yeast alcohol dehydrogenase gene promoter.

15. The DNA construct of claim 11 wherein the heterologous coding sequence encodes a protein selected from the group consisting of luciferase, chloramphenicol acetyl transferase, β-galactosidase, secreted placental alkaline phosphatase, human growth hormone, t-PA, green flourescent protein and interferon.

16. The DNA construct of claim 11 wherein the promoter is a Herpes simplex virus thymidine kinase gene promoter and the heterologous coding sequence encodes luciferase.

17. A cultured or isolated host cell transfected with the DNA construct of claim 11.

18. A DNA construct comprising more than one cytokine-responsive regulatory element operably linked to a promoter, which promoter is operably linked to a heterologous coding sequence, wherein the coding sequence is under the transcriptional control of the regulatory elements and the promoter, and further wherein each regulatory element has a nucleotide sequence selected from the group consisting of TTCNNGAA, TTCNNNNGAA (SEQ ID NO. 7), TTAN$_y$-TAA (SEQ ID NO. 13) and TTCN$_y$TAA (SEQ ID NO. 166), where N is independently selected from A,T,C or G and y is 3 or 4.

19. The DNA construct of claim 18 wherein each regulatory element has the same nucleotide sequence.

* * * * *

SEQUENCE LISTING ( 1 ) GENERAL INFORMATION:

( i i i ) NUMBER OF SEQUENCES: 166

( 2 ) INFORMATION FOR SEQ ID NO:1:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:1:

T T N N N N A A     8

( 2 ) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:2:

T T N N N N N A A     9

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:3:

T T N N N N N N A A     1 0

( 2 ) INFORMATION FOR SEQ ID NO:4:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
            SYNTHETIC DNA"

( x i ) SEQUENCE DESCRIPTION: SEQ ID NO:4:

TTNNNNNNNA A                                                                 11

( 2 ) INFORMATION FOR SEQ ID NO:5:

( i ) SEQUENCE CHARACTERISTICS:
      ( A ) LENGTH: 8 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
            SYNTHETIC DNA"

( x i ) SEQUENCE DESCRIPTION: SEQ ID NO:5:

TTCNNGAA                                                                      8

( 2 ) INFORMATION FOR SEQ ID NO:6:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
            SYNTHETIC DNA"

( x i ) SEQUENCE DESCRIPTION: SEQ ID NO:6:

TTCNNNGAA                                                                     9

( 2 ) INFORMATION FOR SEQ ID NO:7:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
            SYNTHETIC DNA"

( x i ) SEQUENCE DESCRIPTION: SEQ ID NO:7:

TTCNNNNGAA                                                                   10

( 2 ) INFORMATION FOR SEQ ID NO:8:

( i ) SEQUENCE CHARACTERISTICS:
      ( A ) LENGTH: 8 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,

SYNTHETIC DNA"

( x i ) SEQUENCE DESCRIPTION: SEQ ID NO:8:

TTANNGAA                                                                                                              8

( 2 ) INFORMATION FOR SEQ ID NO:9:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:9:

TTANNNGAA                                                                                                             9

( 2 ) INFORMATION FOR SEQ ID NO:10:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:10:

TTANNNNGAA                                                                                                           10

( 2 ) INFORMATION FOR SEQ ID NO:11:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:11:

TTANNNNNGA A                                                                                                         11

( 2 ) INFORMATION FOR SEQ ID NO:12:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:12:

TTANNNTTA                                                                                                             9

( 2 ) INFORMATION FOR SEQ ID NO:13:

( i ) SEQUENCE CHARACTERISTICS:
    ( A ) LENGTH: 10 base pairs
    ( B ) TYPE: nucleic acid ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:13:

T T A N N N N T A A                                                                                         1 0

( 2 ) INFORMATION FOR SEQ ID NO:14:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:14:

T T A N N N N N T A  A                                                                                      1 1

( 2 ) INFORMATION FOR SEQ ID NO:15:

( i ) SEQUENCE CHARACTERISTICS:
            ( A ) LENGTH: 8 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:15:

T T T N N G A A                                                                                             8

( 2 ) INFORMATION FOR SEQ ID NO:16:

( i ) SEQUENCE CHARACTERISTICS:
            ( A ) LENGTH: 9 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:16:

T T T N N N G A A                                                                                           9

( 2 ) INFORMATION FOR SEQ ID NO:17:

( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:17:

T T T N N N N G A A                                                                                         1 0

( 2 ) INFORMATION FOR SEQ ID NO:18:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:18:

T T T N N N N N G A A                     1 1

( 2 ) INFORMATION FOR SEQ ID NO:19:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:19:

T T T N N N T A A                       9

( 2 ) INFORMATION FOR SEQ ID NO:20:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:20:

T T T N N N N T A A                     1 0

( 2 ) INFORMATION FOR SEQ ID NO:21:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:21:

T T T N N N N N T A A                    1 1

( 2 ) INFORMATION FOR SEQ ID NO:22:

( i ) SEQUENCE CHARACTERISTICS:
    ( A ) LENGTH: 8 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:22:

T T C C C G A A                    8

( 2 ) INFORMATION FOR SEQ ID NO:23:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:23:

T T C C C C G A A                    9

( 2 ) INFORMATION FOR SEQ ID NO:24:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:24:

T T C C C C C G A A                    1 0

( 2 ) INFORMATION FOR SEQ ID NO:25:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:25:

T T C C G G A A                    8

( 2 ) INFORMATION FOR SEQ ID NO:26:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:26:

T T C C C G G A A                    9

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:27:

TTCCCCGGAA 10

( 2 ) INFORMATION FOR SEQ ID NO:28:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:28:

TTCCTGGAA 9

( 2 ) INFORMATION FOR SEQ ID NO:29:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:29:

TTCCTTGGAA 10

( 2 ) INFORMATION FOR SEQ ID NO:30:

( i ) SEQUENCE CHARACTERISTICS:
( A ) LENGTH: 8 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:30:

TTCCAGAA 8

( 2 ) INFORMATION FOR SEQ ID NO:31:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:31:

TTCCCAGAA 9

( 2 ) INFORMATION FOR SEQ ID NO:32:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:32:

TTCCCCAGAA   10

( 2 ) INFORMATION FOR SEQ ID NO:33:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:33:

TTCTTTGAA   9

( 2 ) INFORMATION FOR SEQ ID NO:34:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:34:

TTCTTTTGAA   10

( 2 ) INFORMATION FOR SEQ ID NO:35:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:35:

TTCTCAGAA   9

( 2 ) INFORMATION FOR SEQ ID NO:36:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:36:

TTCTCCAGAA 10

(2) INFORMATION FOR SEQ ID NO:37:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:37:

TTACCGTAA 9

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:38:

TTACCCGTAA 10

(2) INFORMATION FOR SEQ ID NO:39:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:39:

TTACCCCGTA A 11

(2) INFORMATION FOR SEQ ID NO:40:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:40:

TTCCCGTAA 9

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "OTHER NUCLEIC ACID, SYNTHETIC DNA"

(x i) SEQUENCE DESCRIPTION: SEQ ID NO:41:

TTCCCCGTAA                                                                                      10

(2) INFORMATION FOR SEQ ID NO:42:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:42:

TTCCCCCGTA A                                                                                    11

(2) INFORMATION FOR SEQ ID NO:43:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:43:

TTCTGTAA                                                                                         8

(2) INFORMATION FOR SEQ ID NO:44:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:44:

TTCTCGTAA                                                                                        9

(2) INFORMATION FOR SEQ ID NO:45:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID, SYNTHETIC DNA"

(x i) SEQUENCE DESCRIPTION: SEQ ID NO:45:

TTCTCCGTAA                                                                                      10

(2) INFORMATION FOR SEQ ID NO:46:

(i) SEQUENCE CHARACTERISTICS:
        (A) LENGTH: 11 base pairs (B) TYPE: nucleic acid
(C) STRANDEDNESS: single
(D) TOPOLOGY: linear (i i) MOLECULE TYPE: other nucleic acid
(A) DESCRIPTION: /desc = "OTHER NUCLEIC ACID, SYNTHETIC DNA"

(x i) SEQUENCE DESCRIPTION: SEQ ID NO:46:

TTCTCCCGTA A                                                                 11

(2) INFORMATION FOR SEQ ID NO:47:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OTHER NUCLEIC ACID, SYNTHETIC DNA"

(x i) SEQUENCE DESCRIPTION: SEQ ID NO:47:

TTCCCAAGAA                                                                   10

(2) INFORMATION FOR SEQ ID NO:48:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OTHER NUCLEIC ACID, SYNTHETIC DNA"

(x i) SEQUENCE DESCRIPTION: SEQ ID NO:48:

TTTCCCGTAA                                                                   10

(2) INFORMATION FOR SEQ ID NO:49:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OTHER NUCLEIC ACID, SYNTHETIC DNA"

(x i) SEQUENCE DESCRIPTION: SEQ ID NO:49:

TTCCCAGGAA                                                                   10

(2) INFORMATION FOR SEQ ID NO:50:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OTHER NUCLEIC ACID, SYNTHETIC DNA"

(x i) SEQUENCE DESCRIPTION: SEQ ID NO:50:

TTCTTAAGAA                                                                   10

( 2 ) INFORMATION FOR SEQ ID NO:51:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:51:

T T C T A A G A A         9

( 2 ) INFORMATION FOR SEQ ID NO:52:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:52:

T T T C C C C G A A         1 0

( 2 ) INFORMATION FOR SEQ ID NO:53:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:53:

T T T C T A A G A A         1 0

( 2 ) INFORMATION FOR SEQ ID NO:54:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:54:

G A T C T G C T T C   C G A A C G T         1 7

( 2 ) INFORMATION FOR SEQ ID NO:55:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:55:

GATCACGTTC GGAAGCA  17

( 2 ) INFORMATION FOR SEQ ID NO:56:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:56:

GATCTGCTTC CCGAACGT  18

( 2 ) INFORMATION FOR SEQ ID NO:57:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:57:

GATCACGTTC GGGAAGCA  18

( 2 ) INFORMATION FOR SEQ ID NO:58:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:58:

GATCTGCTTC CCCGAACGT  19

( 2 ) INFORMATION FOR SEQ ID NO:59:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:59:

GATCACGTTC GGGGAAGCA  19

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (i i) MOLECULE TYPE: other nucleic acid
  (A) DESCRIPTION: /desc = "OTHER NUCLEIC ACID, SYNTHETIC DNA"

(x i) SEQUENCE DESCRIPTION: SEQ ID NO:60:

GATCTGCTTC CCCCGAACGT 20

(2) INFORMATION FOR SEQ ID NO:61:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "OTHER NUCLEIC ACID, SYNTHETIC DNA"

(x i) SEQUENCE DESCRIPTION: SEQ ID NO:61:

GATCACGTTC GGGGGAAGCA 20

(2) INFORMATION FOR SEQ ID NO:62:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "OTHER NUCLEIC ACID, SYNTHETIC DNA"

(x i) SEQUENCE DESCRIPTION: SEQ ID NO:62:

GATCTGCTTC CCCCCGAACG T 21

(2) INFORMATION FOR SEQ ID NO:63:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "OTHER NUCLEIC ACID, SYNTHETIC DNA"

(x i) SEQUENCE DESCRIPTION: SEQ ID NO:63:

GATCACGTTC GGGGGGAAGC A 21

(2) INFORMATION FOR SEQ ID NO:64:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "OTHER NUCLEIC ACID, SYNTHETIC DNA"

(x i) SEQUENCE DESCRIPTION: SEQ ID NO:64:

GATCTGCTTC CCCCCCGAAC GT 22

(2) INFORMATION FOR SEQ ID NO:65:

( i ) SEQUENCE CHARACTERISTICS:
- ( A ) LENGTH: 22 base pairs
- ( B ) TYPE: nucleic acid
- ( C ) STRANDEDNESS: single
- ( D ) TOPOLOGY: linear ( i i ) MOLECULE TYPE: other nucleic acid
- ( A ) DESCRIPTION: /desc = "OTHER NUCLEIC ACID, SYNTHETIC DNA"

( x i ) SEQUENCE DESCRIPTION: SEQ ID NO:65:

GATCACGTTC GGGGGGGAAG CA            22

( 2 ) INFORMATION FOR SEQ ID NO:66:

( i ) SEQUENCE CHARACTERISTICS:
- ( A ) LENGTH: 18 base pairs
- ( B ) TYPE: nucleic acid
- ( C ) STRANDEDNESS: single
- ( D ) TOPOLOGY: linear ( i i ) MOLECULE TYPE: other nucleic acid
- ( A ) DESCRIPTION: /desc = "OTHER NUCLEIC ACID, SYNTHETIC DNA"

( x i ) SEQUENCE DESCRIPTION: SEQ ID NO:66:

GATCTGCTTC CGGAACGT            18

( 2 ) INFORMATION FOR SEQ ID NO:67:

( i ) SEQUENCE CHARACTERISTICS:
- ( A ) LENGTH: 18 base pairs
- ( B ) TYPE: nucleic acid
- ( C ) STRANDEDNESS: single
- ( D ) TOPOLOGY: linear ( i i ) MOLECULE TYPE: other nucleic acid
- ( A ) DESCRIPTION: /desc = "OTHER NUCLEIC ACID, SYNTHETIC DNA"

( x i ) SEQUENCE DESCRIPTION: SEQ ID NO:67:

GATCACGTTC CGGAAGCA            18

( 2 ) INFORMATION FOR SEQ ID NO:68:

( i ) SEQUENCE CHARACTERISTICS:
- ( A ) LENGTH: 19 base pairs
- ( B ) TYPE: nucleic acid
- ( C ) STRANDEDNESS: single
- ( D ) TOPOLOGY: linear ( i i ) MOLECULE TYPE: other nucleic acid
- ( A ) DESCRIPTION: /desc = "OTHER NUCLEIC ACID, SYNTHETIC DNA"

( x i ) SEQUENCE DESCRIPTION: SEQ ID NO:68:

GATCTGCTTC CCGGAACGT            19

( 2 ) INFORMATION FOR SEQ ID NO:69:

( i ) SEQUENCE CHARACTERISTICS:
- ( A ) LENGTH: 19 base pairs
- ( B ) TYPE: nucleic acid
- ( C ) STRANDEDNESS: single
- ( D ) TOPOLOGY: linear ( i i ) MOLECULE TYPE: other nucleic acid
- ( A ) DESCRIPTION: /desc = "OTHER NUCLEIC ACID, SYNTHETIC DNA"

( x i ) SEQUENCE DESCRIPTION: SEQ ID NO:69:

```
GATCACGTTC CGGGAAGCA                                                                              19
```

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:70:

```
GATCTGCTTC CCCGGAACGT                                                                             20
```

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:71:

```
GATCACGTTC CGGGGAAGCA                                                                             20
```

(2) INFORMATION FOR SEQ ID NO:72:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:72:

```
GATCTGCTTC CCCCGGAACG T                                                                           21
```

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:73:

```
GATCACGTTC CGGGGGAAGC A                                                                           21
```

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear ( i i ) MOLECULE TYPE: other nucleic acid
  ( A ) DESCRIPTION: /desc = "OTHER NUCLEIC ACID, SYNTHETIC DNA"

( x i ) SEQUENCE DESCRIPTION: SEQ ID NO:74:

GATCTGCTTC CCCCCGGAAC GT                       22

( 2 ) INFORMATION FOR SEQ ID NO:75:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:75:

GATCACGTTC CGGGGGGAAG CA                       22

( 2 ) INFORMATION FOR SEQ ID NO:76:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:76:

GATCTGCTTC CTGGAACGT                           19

( 2 ) INFORMATION FOR SEQ ID NO:77:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:77:

GATCACGTTC CAGGAAGCA                           19

( 2 ) INFORMATION FOR SEQ ID NO:78:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:78:

GATCTGCTTC CTTGGAACGT                          20

( 2 ) INFORMATION FOR SEQ ID NO:79:

( i ) SEQUENCE CHARACTERISTICS:

```
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:79:

GATCACGTTC  CAAGGAAGCA                                                                      20

( 2 ) INFORMATION FOR SEQ ID NO:80:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:80:

GATCTGCTTC  CTTTGGAACG  T                                                                   21

( 2 ) INFORMATION FOR SEQ ID NO:81:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:81:

GATCACGTTC  CAAAGGAAGC  A                                                                   21

( 2 ) INFORMATION FOR SEQ ID NO:82:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:82:

GATCTGCTTC  CAGAACGT                                                                        18

( 2 ) INFORMATION FOR SEQ ID NO:83:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OTHER NUCLEIC ACID,
                    SYNTHETIC DNA"

( x i ) SEQUENCE DESCRIPTION: SEQ ID NO:83:

GATCACGTTC  TGGAAGCA                                                                        18
```

( 2 ) INFORMATION FOR SEQ ID NO:84:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:84:

GATCTGCTTC CCAGAACGT      19

( 2 ) INFORMATION FOR SEQ ID NO:85:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:85:

GATCACGTTC TGGGAAGCA      19

( 2 ) INFORMATION FOR SEQ ID NO:86:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:86:

GATCTGCTTC CCCAGAACGT      20

( 2 ) INFORMATION FOR SEQ ID NO:87:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID,
      SYNTHETIC DNA"

( x i ) SEQUENCE DESCRIPTION: SEQ ID NO:87:

GATCACGTTC TGGGGAAGCA      20

( 2 ) INFORMATION FOR SEQ ID NO:88:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, 5,814,517

( x i ) SEQUENCE DESCRIPTION: SEQ ID NO:88:

GATCTGCTTC CCCCAGAACG T                                             21

( 2 ) INFORMATION FOR SEQ ID NO:89:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:89:

GATCACGTTC TGGGGGAAGC A                                             21

( 2 ) INFORMATION FOR SEQ ID NO:90:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:90:

GATCTGCTTC TTGAACGT                                                 18

( 2 ) INFORMATION FOR SEQ ID NO:91:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:91:

GATCACGTTC AAGAAGCA                                                 18

( 2 ) INFORMATION FOR SEQ ID NO:92:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:92:

GATCTGCTTC TTTGAACGT                                                19

( 2 ) INFORMATION FOR SEQ ID NO:93:

( i ) SEQUENCE CHARACTERISTICS:
        ( A ) LENGTH: 19 base pairs
        ( B ) TYPE: nucleic acid ( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:93:

GATCACGTTC AAAGAAGCA 19

( 2 ) INFORMATION FOR SEQ ID NO:94:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:94:

GATCTGCTTC TTTTGAACGT 20

( 2 ) INFORMATION FOR SEQ ID NO:95:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:95:

GATCACGTTC AAAAGAAGCA 20

( 2 ) INFORMATION FOR SEQ ID NO:96:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:96:

GATCTGCTTC TTTTTGAACG T 21

( 2 ) INFORMATION FOR SEQ ID NO:97:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "OTHER NUCLEIC ACID, SYNTHETIC DNA"

( x i ) SEQUENCE DESCRIPTION: SEQ ID NO:97:

GATCACGTTC AAAAAGAAGC A 21

( 2 ) INFORMATION FOR SEQ ID NO:98:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:98:

GATCTGCTTC TAGAACGT        18

( 2 ) INFORMATION FOR SEQ ID NO:99:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:99:

GATCACGTTC TAGAAGCA        18

( 2 ) INFORMATION FOR SEQ ID NO:100:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:100:

GATCTGCTTC TCAGAACGT        19

( 2 ) INFORMATION FOR SEQ ID NO:101:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:101:

GATCACGTTC TGAGAAGCA        19

( 2 ) INFORMATION FOR SEQ ID NO:102:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:102:

GATCTGCTTC TCCAGAACGT 20

( 2 ) INFORMATION FOR SEQ ID NO:103:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:103:

GATCACGTTC TGGAGAAGCA 20

( 2 ) INFORMATION FOR SEQ ID NO:104:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:104:

GATCTGCTTC TCCCAGAACG T 21

( 2 ) INFORMATION FOR SEQ ID NO:105:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:105:

GATCACGTTC TGGGAGAAGC A 21

( 2 ) INFORMATION FOR SEQ ID NO:106:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:106:

GATCGATTTC CCCGAAATG 19

( 2 ) INFORMATION FOR SEQ ID NO:107:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
  ( A ) DESCRIPTION: /desc = "OTHER NUCLEIC ACID,
      SYNTHETIC DNA"

( x i ) SEQUENCE DESCRIPTION: SEQ ID NO:107:

GATCCATTTC GGGGAAATC                    19

( 2 ) INFORMATION FOR SEQ ID NO:108:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
          SYNTHETIC DNA"

( x i ) SEQUENCE DESCRIPTION: SEQ ID NO:108:

GATCCAATTT CTAAGAAAGG A                 21

( 2 ) INFORMATION FOR SEQ ID NO:109:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
          SYNTHETIC DNA"

( x i ) SEQUENCE DESCRIPTION: SEQ ID NO:109:

GATCTCCTTT CTTAGAAATT G                 21

( 2 ) INFORMATION FOR SEQ ID NO:110:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
          SYNTHETIC DNA"

( x i ) SEQUENCE DESCRIPTION: SEQ ID NO:110:

GATCCACTTC CCAAGAACAG A                 21

( 2 ) INFORMATION FOR SEQ ID NO:111:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "OTHER NUCLEIC ACID,
          SYNTHETIC DNA"

( x i ) SEQUENCE DESCRIPTION: SEQ ID NO:111:

GATCTCTGTT CTTGGGAAGT G                 21

( 2 ) INFORMATION FOR SEQ ID NO:112:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "OTHER NUCLEIC ACID, SYNTHETIC DNA"

(xi) SEQUENCE DESCRIPTION: SEQ ID NO:112:

GATCTGCTTA CGTAACGT 18

(2) INFORMATION FOR SEQ ID NO:113:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:113:

GATCACGTTA CGTAAGCA 18

(2) INFORMATION FOR SEQ ID NO:114:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:114:

GATCTGCTTA CCGTAACGT 19

(2) INFORMATION FOR SEQ ID NO:115:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:115:

GATCACGTTA CGGTAAGCA 19

(2) INFORMATION FOR SEQ ID NO:116:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OTHER NUCLEIC ACID, SYNTHETIC DNA"

(xi) SEQUENCE DESCRIPTION: SEQ ID NO:116:

GATCTGCTTA CCCGTAACGT 20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:117:

GATCACGTTA CGGGTAAGCA 20

(2) INFORMATION FOR SEQ ID NO:118:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:118:

GATCTGCTTA CCCCGTAACG T 21

(2) INFORMATION FOR SEQ ID NO:119:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:119:

GATCACGTTA CGGGGTAAGC A 21

(2) INFORMATION FOR SEQ ID NO:120:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID, SYNTHETIC DNA"

(xi) SEQUENCE DESCRIPTION: SEQ ID NO:120:

GATCTGCTTC CGTAACGT 18

(2) INFORMATION FOR SEQ ID NO:121:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid ( A ) DESCRIPTION: /desc = "OTHER NUCLEIC ACID,
 SYNTHETIC DNA"

( x i ) SEQUENCE DESCRIPTION: SEQ ID NO:121:

GATCACGTTA CGGAAGCA 18

( 2 ) INFORMATION FOR SEQ ID NO:122:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
          SYNTHETIC DNA"

( x i ) SEQUENCE DESCRIPTION: SEQ ID NO:122:

GATCTGCTTC CCGTAACGT 19

( 2 ) INFORMATION FOR SEQ ID NO:123:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
          SYNTHETIC DNA"

( x i ) SEQUENCE DESCRIPTION: SEQ ID NO:123:

GATCACGTTA CGGGAAGCA 19

( 2 ) INFORMATION FOR SEQ ID NO:124:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
          SYNTHETIC DNA"

( x i ) SEQUENCE DESCRIPTION: SEQ ID NO:124:

GATCTGCTTC CCCGTAACGT 20

( 2 ) INFORMATION FOR SEQ ID NO:125:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
          SYNTHETIC DNA"

( x i ) SEQUENCE DESCRIPTION: SEQ ID NO:125:

GATCACGTTA CGGGGAAGCA 20

( 2 ) INFORMATION FOR SEQ ID NO:126:

( i ) SEQUENCE CHARACTERISTICS:
        ( A ) LENGTH: 21 base pairs (B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:126:

GATCTGCTTC CCCCGTAACG T     21

(2) INFORMATION FOR SEQ ID NO:127:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:127:

GATCACGTTA CGGGGGAAGC A     21

(2) INFORMATION FOR SEQ ID NO:128:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:128:

GATCTGCTTC TGTAACGT     18

(2) INFORMATION FOR SEQ ID NO:129:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:129:

GATCACGTTA CAGAAGCA     18

(2) INFORMATION FOR SEQ ID NO:130:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:130:

GATCTGCTTC TCGTAACGT     19

( 2 ) INFORMATION FOR SEQ ID NO:131:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:131:

GATCACGTTA CGAGAAGCA                                              19

( 2 ) INFORMATION FOR SEQ ID NO:132:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:132:

GATCTGCTTC TCCGTAACGT                                           20

( 2 ) INFORMATION FOR SEQ ID NO:133:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:133:

GATCACGTTA CGGAGAAGCA                                           20

( 2 ) INFORMATION FOR SEQ ID NO:134:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:134:

GATCTGCTTC TCCCGTAACG T                                         21

( 2 ) INFORMATION FOR SEQ ID NO:135:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID,
            SYNTHETIC DNA"

( x i ) SEQUENCE DESCRIPTION: SEQ ID NO:135:

GATCACGTTA CGGGAGAAGC A 21

( 2 ) INFORMATION FOR SEQ ID NO:136:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:136:

GATCTGCTTC CCAAGAACGT 20

( 2 ) INFORMATION FOR SEQ ID NO:137:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:137:

GATCACGTTC TTGGGAAGCA 20

( 2 ) INFORMATION FOR SEQ ID NO:138:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:138:

GATCCACTTC CCCGGAACAG A 21

( 2 ) INFORMATION FOR SEQ ID NO:139:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:139:

GATCTCTGTT CCGGGGAAGT G 21

( 2 ) INFORMATION FOR SEQ ID NO:140:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (i i) MOLECULE TYPE: other nucleic acid
    (A) DESCRIPTION: /desc = "OTHER NUCLEIC ACID,
        SYNTHETIC DNA"

(x i) SEQUENCE DESCRIPTION: SEQ ID NO:140:

GATCCACTTC CCCAGAACAG A                                    21

(2) INFORMATION FOR SEQ ID NO:141:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:141:

GATCTCTGTT CTGGGGAAGT G                                    21

(2) INFORMATION FOR SEQ ID NO:142:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:142:

GATCCACTTC CCAGGAACAG A                                    21

(2) INFORMATION FOR SEQ ID NO:143:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:143:

GATCTCTGTT CCTGGGAAGT G                                    21

(2) INFORMATION FOR SEQ ID NO:144:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:144:

GATCTACTTC CCAAGAACAT A                                    21

(2) INFORMATION FOR SEQ ID NO:145:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "OTHER NUCLEIC ACID, SYNTHETIC DNA"

( x i ) SEQUENCE DESCRIPTION: SEQ ID NO:145:

GATCTATGTT CTTGGGAAGT A                    21

( 2 ) INFORMATION FOR SEQ ID NO:146:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:146:

GATCCGCTTC CCAAGAACGG A                    21

( 2 ) INFORMATION FOR SEQ ID NO:147:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:147:

GATCTCCGTT CTTGGGAAGC G                    21

( 2 ) INFORMATION FOR SEQ ID NO:148:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:148:

GATCCACTTC TTAAGAACAG A                    21

( 2 ) INFORMATION FOR SEQ ID NO:149:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OTHER NUCLEIC ACID, SYNTHETIC DNA"

( x i ) SEQUENCE DESCRIPTION: SEQ ID NO:149:

GATCTCTGTT CTTAAGAAGT G                                    21

( 2 ) INFORMATION FOR SEQ ID NO:150:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:150:

GATCCACTTT CCAAGAACAG A                                    21

( 2 ) INFORMATION FOR SEQ ID NO:151:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:151:

GATCTCTGTT CTTGGAAAGT G                                    21

( 2 ) INFORMATION FOR SEQ ID NO:152:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:152:

ANTTCNNNNG AANA                                            14

( 2 ) INFORMATION FOR SEQ ID NO:153:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OTHER NUCLEIC ACID, SYNTHETIC DNA"

( x i ) SEQUENCE DESCRIPTION: SEQ ID NO:153:

TNTTCNNNNG AANT                                            14

( 2 ) INFORMATION FOR SEQ ID NO:154:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
                ( A ) DESCRIPTION: /desc = "OTHER NUCLEIC ACID,
                      SYNTHETIC DNA"

( x i ) SEQUENCE DESCRIPTION: SEQ ID NO:154:

ACTTCCCAAG AACA                                                                                  14

( 2 ) INFORMATION FOR SEQ ID NO:155:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "OTHER NUCLEIC ACID,
                      SYNTHETIC DNA"

( x i ) SEQUENCE DESCRIPTION: SEQ ID NO:155:

TGTTCTTGGG AAGT                                                                                  14

( 2 ) INFORMATION FOR SEQ ID NO:156:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "OTHER NUCLEIC ACID,
                      SYNTHETIC DNA"

( x i ) SEQUENCE DESCRIPTION: SEQ ID NO:156:

ACTTCCCCGG AACA                                                                                  14

( 2 ) INFORMATION FOR SEQ ID NO:157:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "OTHER NUCLEIC ACID,
                      SYNTHETIC DNA"

( x i ) SEQUENCE DESCRIPTION: SEQ ID NO:157:

TGTTCCGGGG AAGT                                                                                  14

( 2 ) INFORMATION FOR SEQ ID NO:158:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "OTHER NUCLEIC ACID,
                      SYNTHETIC DNA"

( x i ) SEQUENCE DESCRIPTION: SEQ ID NO:158:

ACTTCCCCAG AACA                                                                                  14

( 2 ) INFORMATION FOR SEQ ID NO:159:

( i ) SEQUENCE CHARACTERISTICS:

(A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:159:

TGTTCTGGGG AAGT 14

(2) INFORMATION FOR SEQ ID NO:160:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:160:

ACTTCCCAGG AACA 14

(2) INFORMATION FOR SEQ ID NO:161:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:161:

TGTTCCTGGG AAGT 14

(2) INFORMATION FOR SEQ ID NO:162:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:162:

ACTTCCCAAG AACA 14

(2) INFORMATION FOR SEQ ID NO:163:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "OTHER NUCLEIC ACID,
            SYNTHETIC DNA"

(x i) SEQUENCE DESCRIPTION: SEQ ID NO:163:

TGTTCTTGGG AAGT 14

(2) INFORMATION FOR SEQ ID NO:164:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:164:

ACTTCTTAAG AACA                                                                                             14

(2) INFORMATION FOR SEQ ID NO:165:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:165:

TGTTCTTAAG AAGT                                                                                             14

(2) INFORMATION FOR SEQ ID NO:166:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OTHER NUCLEIC ACID, SYNTHETIC DNA"

(xi) SEQUENCE DESCRIPTION: SEQ ID NO:166:

TTCNNNNTAA                                                                                                  10